(12) United States Patent
Frutos et al.

(10) Patent No.: US 8,653,282 B2
(45) Date of Patent: Feb. 18, 2014

(54) PREPARATION OF DIHYDROTHIENO [3,2-D] PYRIMIDINES AND INTERMEDIATES USED THEREIN

(75) Inventors: Rogelio Frutos, Sandy Hook, CT (US); Dhileepkumar Krishnamurthy, Brookfield, CT (US); Jason Alan Mulder, New Milford, CT (US); Sonia Rodriguez, New Milford, CT (US); Chris Hugh Senanayake, Brookfield, CT (US); Thomas G. Tampone, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 433 days.

(21) Appl. No.: 12/738,152

(22) PCT Filed: Oct. 15, 2008

(86) PCT No.: PCT/US2008/079925
§ 371 (c)(1),
(2), (4) Date: May 18, 2010

(87) PCT Pub. No.: WO2009/052138
PCT Pub. Date: Apr. 23, 2009

(65) Prior Publication Data
US 2010/0222585 A1 Sep. 2, 2010

Related U.S. Application Data

(60) Provisional application No. 60/981,105, filed on Oct. 18, 2007.

(51) Int. Cl.
*C07D 333/32* (2006.01)
*C07D 495/04* (2006.01)

(52) U.S. Cl.
USPC ............................................ 549/64; 544/278

(58) Field of Classification Search
USPC ........................................................ 549/64
See application file for complete search history.

(56) References Cited

U.S. PATENT DOCUMENTS

| | | | |
|---|---|---|---|
| 3,318,881 A | 5/1967 | Ohnacker et al. | |
| 4,242,518 A | 12/1980 | Rossy et al. | |
| 4,974,609 A | 12/1990 | Southwick et al. | |
| 6,441,195 B1 | 8/2002 | Muller et al. | |
| 7,723,341 B2 | 5/2010 | Hoenke et al. | |
| 8,114,878 B2 | 2/2012 | Pouzet et al. | |
| 2010/0298361 A1 | 11/2010 | Ly | |
| 2011/0021501 A1 | 1/2011 | Pouzet et al. | |

FOREIGN PATENT DOCUMENTS

| | | |
|---|---|---|
| CA | 2236208 | 9/1997 |
| CA | 2605161 | 10/2006 |
| DE | 2700215 | 7/1979 |
| DE | 19540737 A1 | 5/1997 |
| WO | 9510506 A1 | 4/1995 |
| WO | 2006111549 A1 | 10/2006 |
| WO | 2009050248 A1 | 4/2009 |

OTHER PUBLICATIONS

Urabe et al., Lewis Acids in Organic Synthesis, Chapter 15, Titanium (IV) Lewis Acids, 2000, pp. 653-798).*
Desmukh et al.; Regioselective titanium tetrachloride mediated five membered hetero-cyclizations; Synthetic Communications; 1996; vol. 26; No. 9; pp. 1657-1661.
International Search Report, Form PCT/ISA/210, for corresponding PCT/US2008/079925; date of mailing: Mar. 26, 2009.
Correa, Carlos; Guideles for the Examination of Pharmaceutical Patents: Developing a Public Health Perspective; ICTSD—UNCTAD—WHO (2007) pp. 12-14.
Katritzky, Alan, R., et al; Regioselectivity of the Reactions of Heteroatom-Stabilized Allyl Anions with Elestrophiles; published Jan. 20, 1998, pp. 665-722.

* cited by examiner

*Primary Examiner* — Susanna Moore
(74) *Attorney, Agent, or Firm* — Michael P. Morris; Timothy X. Witkowski

(57) ABSTRACT

The invention relates to improved methods of preparing dihydrothienopyrimidines of formula 1, and intermediates thereof, (I) wherein X is SO or $SO_2$, preferably SO, and wherein $R_A$, $R^1$, $R^2$, $R^3$, $R^4$ and $R^5$ have the meanings given in the description. The methods according to this invention are more suitable for large-scale synthesis of said compounds than prior methods because the new synthetic process avoids distillation and chromatographic purification between steps and results in a higher overall yield of the desired product.

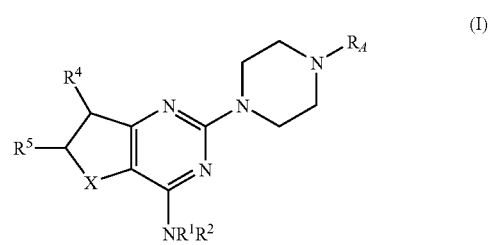

(I)

11 Claims, No Drawings

PREPARATION OF DIHYDROTHIENO [3,2-D] PYRIMIDINES AND INTERMEDIATES USED THEREIN

This application is a national phase entry under 35 U.S.C. 371 of international application PCT/US2008/079925, filed Oct. 15, 2008, which claims priority to U.S. Application Ser. No. 60/981,105, filed Oct. 18, 2007, each of which is hereby incorporated by reference in its entirety.

CROSS-REFERENCE TO RELATED APPLICATIONS

This application claims benefit to U.S. Provisional Application No. 60/981,105, filed Oct. 18, 2007, the content of which is hereby incorporated by reference.

FIELD OF THE INVENTION

The invention relates to improved methods of preparing dihydrothienopyrimidines and intermediate compounds used therein.

DESCRIPTION OF RELATED ART

Dihydrothienopyrimidines are known to have therapeutic activity that may make them suitable for treating various diseases or symptoms thereof. For example, U.S. Pat. No. 3,318,881 and BE 663693 disclose the preparation of dihydrothieno[3,2-d]pyrimidines which have cardiovascular and sedative properties. U.S. publication no. 2008/0096882A1, hereby incorporated by reference, discloses dihydrothienopyrimidines that are suitable for the treatment of respiratory or gastrointestinal complaints or diseases, inflammatory diseases of the joints, skin or eyes, diseases of the peripheral or central nervous system or cancers.

The synthesis of a dihydrothienopyrimidine involves multiple steps and can result in issues associated with stereoselectivity, regioselectivity and purification, especially on a large-scale. Intermediates such as 3-oxo-tetrahydrothiophene-2-carboxylic acid esters may be used in an early step of this synthesis. Traditional syntheses of 3-oxo-tetrahydrothiophene-2-carboxylic acid esters involve controlled Dieckmann type condensations under basic conditions, e.g., NaH and NaOMe (Yamada et al., *Tetrahedron Lett.* 1981, 22, 1353). However, the use of ordinary diesters for a base-promoted Dieckmann condensation is reported to occur without selectivity and thus, affords a mixture of regioisomers (see Equation 1 below).

(Eqn. 1)

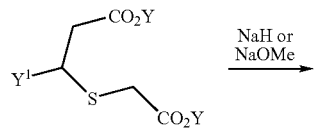

a1, $Y^1$ = H
Y = Me

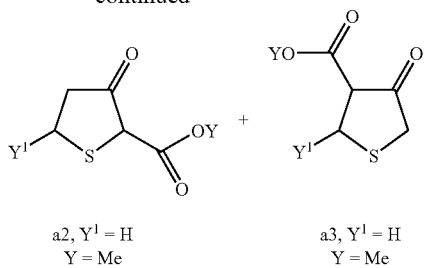

a2, $Y^1$ = H
Y = Me a3, $Y^1$ = H
Y = Me

As a result, isolation of a single regiostereomer to be used in additional synthetic steps requires further separation by silica gel chromatography. See, e.g., Liu et al., *Can. J. Chem.* 1982, 60, 437 and Li et al., *Bioorg. Med. Chem. Lett.* 2003, 13, 2591. The regioselective formation of a2 from a1 by $TiCl_4$ in the presence of $Et_3N$ has been reported (Deshmukh, et al., *Synth. Commun.*, 1996, 26, 1657). However, this transformation results in the simultaneous formation of impurities arising from chlorination and dehydrohalogenation, which necessitates removal by silica gel chromatography. Additionally, any workup procedure may result in the formation of vast quantities of solids that have to be removed by labor intensive filtration steps. Likewise, the use of excess $Et_3N$ causes decomposition of the product upon scale-up. As a result of these issues, $TiCl_4$ promoted condensation is impractical for large-scale manufacturing. The need to develop a practical and regioselective synthesis of 3-oxo-tetrahydrothiophene-2-carboxylic acid ester thus remains.

Similarly, the entire synthetic process for preparing dihydrothienopyrimidines may be cumbersome due to the need for multiple purifications, microwave irradiation and control of highly exothermic reactions. Thus, a need to optimize reaction conditions and reduce the number of process steps in synthesizing dihydrothienopyrimidines, particularly for large-scale preparation, also remains.

BRIEF DESCRIPTION OF THE INVENTION

The invention discussed herein solves the problem of regioselectivity, and eliminates (a) purification of intermediates, (b) use of microwave irradiation in reaction steps and (c) highly exothermic reactions, in preparing dihydrothienopyrimidines. In one aspect, the present invention reduces the number of synthetic steps to prepare dihydrothienopyrimidine compounds of formula 1:

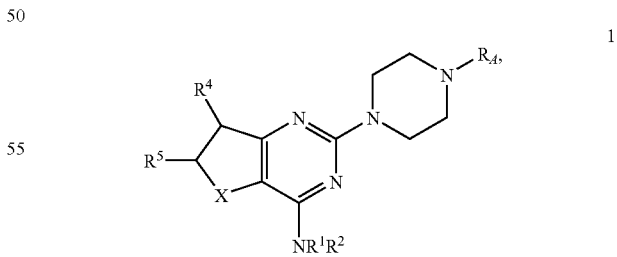

wherein:
$R_A$ denotes a residue selected from among the group consisting of Het, Hetaryl and, which is optionally substituted by a residue selected from the group consisting of halogen, $C_{1-3}$-fluoroalkyl, CN, OH, Oxo, —$C_{1-6}$-Alkyl, —O—$R^{2.1}$, —$COOR^2SO$—$R^{2.1}$, $SO_2$—$R^{2.1}$, $C_{6-10}$ Aryl, $C_{1-3}$-alkylene-$C_{6-10}$-Aryl, —$C_{1-3}$-alkylene-$NR^{2.2}R^{2.3}$, —$NR^{2.2}R^{2.3}$, $C_{3-10}$-cycloalkyl, $C_{1-3}$-alkylen-$C_{3-10}$-cycloalkyl, Het, Hetaryl, $C_{1-3}$-alkylen-Hetaryl, and $C_{1-3}$-alkylen-Het, which may optionally be substituted by a residue selected form among OH, Halogen, —$C_{1-3}$-Fluoroalkyl, $C_{1-6}$-Alkyl, $C_{6-10}$-Aryl, —COO($C_{1-3}$-Alkyl) and O—($C_{1-3}$-Alkyl), with Het being a three- to eleven-membered, mono- or bicyclic, saturated or partially saturated heterocyclus which contains 1, 2, 3 or 4 heteroatoms which are independently selected from among N, S or O, Hetaryl being a five- to eleven-membered, mono- or bicyclic heteroaryl which contains 1, 2, 3 or 4 heteroatoms which are independently selected from among N, S or O, with cycloalkyl being saturated or partially saturated, or wherein $R_A$ denotes

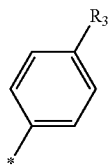

and wherein

X denotes SO or $SO_2$, preferably SO;

$R^1$ denotes H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene or $C_{5-10}$-heteroaryl-$C_{1-6}$-alkylene;

$R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$, while $R^{2.1}$ is H or a group selected from among $C_{1-6}$-alkyl, $C_{1-6}$-alkanol, $C_{1-3}$-haloalkyl, mono- or bicyclic $C_{3-10}$ cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl, while $R^{2.2}$ and $R^{2.3}$ independently of one another are H or a group selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$ heterocycle, mono- or bicyclic $C_{5-10}$-heteroaryl, $CO$—$NH_2$, $CO$—$NHCH_3$, $CO$—$N(CH_3)_2$, $SO_2(C_1$-$C_2$-alkyl), $CO$—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{3-10}$ cycloalkyl, which may optionally be bridged by one or more $C_{1-3}$-alkyl groups and which may optionally be substituted by a group selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1-6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono- or bicyclic, saturated or unsaturated $C_{3-10}$ heterocycle and a mono- or bicyclic $C_{5-10}$-heteroaryl, which includes 1 to 4 heteroatoms selected from among S, O and N and optionally by one or more groups selected from among halogen, OH, oxo and SH or by one or more groups selected from among $OR^{2.1}$, $SR^{2.1}$, $COOR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, $C_{5-40}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl, $CH_2$—$NR^{2.2}R^{2.3}$ and $NR^{2.2}R^{2.3}$;

or wherein, $NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—$COO$—$R^{2.1}$, $CH_2$—$NR^{2.2}$—$CO$—$R^{2.1}$, $CH_2$—$NR^{2.2}$—$CO$—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—$CO$—$NR^{2.2}R^{2.3}$, $CO$—$NR^{2.2}R^{2.3}$ and $NR^{2.2}R^{2.3}$;

$R^3$ is selected from among fluorine, chlorine, bromine, iodine, hydroxy, $SO_2$—$CH_3$, $COOR^{2.1}$, nitrile group and $C_{3-10}$ heterocycle-$C_{1-6}$-alkylene, wherein the $C_{3-10}$ heterocycle may be mono- or bicyclic and may optionally be substituted by a group selected from among OH, halogen, oxo, $C_{1-6}$-alkyl and $C_{6-10}$-aryl, or is a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{3-10}$ heterocycle and $C_{3-10}$-cycloalkyl, which may optionally be substituted by a group selected from among OH, halogen, oxo, $C_{1-6}$-alkyl and $C_{6-10}$-aryl, or $R^3$ denotes the group —$CO$—$NR^{3.1}R^{3.2}$, wherein $R^{3.1}$ and $R^{3.2}$ independently of one another are H or groups selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{3-10}$ heterocycle, $C_{3-10}$ heterocycle-$C_{1-6}$-alkylene and mono- or bicyclic $C_{5-10}$-heteroaryl, wherein the group in each case may optionally be substituted by one or more groups selected from among OH, oxo, halogen, $C_{1-6}$-alkyl and O—$C_{1-6}$-alkyl, or $R^3$ denotes the group —$NR^{3.3}$—CO—$R^{3.4}$,
wherein $R^{3.3}$ is H or a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{3-10}$ heterocycle and a $C_{5-10}$-heteroaryl, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, and wherein $R^{3.4}$ is H or a group selected from among $C_{1-6}$-alkyl, $C_{2-6}$-alkenyl, $C_{2-6}$-alkynyl, $C_{1-6}$-alkanol, $OR^{2.1}$, $CH_2$—O—CO—$C_{1-6}$-alkyl, $CH_2$—$NR^{2.2}R^{2.3}$, $NR^{2.2}R^{2.3}$, $C_{6-10}$-aryl; $C_{6-10}$-aryl-$C_{1-6}$-alkylene, $C_{5-10}$-heteroaryl-$C_{1-6}$-alkylene, mono- or bicyclic, saturated, partially saturated or unsaturated $C_{3-10}$ heterocycle with 1, 2 or 3 heteroatoms selected from among S, O and N and a mono- or bicyclic $C_{5-10}$-heteroaryl with 1, 2 or 3 heteroatoms selected from among S, O and N, which may optionally be substituted by one or more groups selected from among OH, $OR^{2.1}$, oxo, $NH_2$, $NR^{2.1}R^{2.3}$, halogen, $C_{1-6}$-alkyl and $C_{6-10}$-aryl, or $R^3$ denotes an optionally mono- or di-N-substituted sulphonamide group $SO_2$—$NR^{3.5}R^{3.6}$,
wherein $R^{3.5}$ and $R^{3.6}$ may each independently of one another be $C_{1-6}$-alkyl or $C_{6-10}$-aryl;

and $R^4$ and $R^5$ are independently selected from H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{5-10}$-heteroaryl-$C_{1-6}$-alkylene, $C_{3-10}$ heterocycle and a $C_{5-10}$-heteroaryl, —O—$C_{1-6}$-alkyl, —O—$C_{6-10}$-aryl, —O—$C_{3-10}$ heterocycle and —O—$C_{5-10}$-heteroaryl, —NR'R", fluoro, $C_{1-6}$-fluoroalkyl, and $C_{1-6}$-fluoroalkoxy, wherein R' and R" are independently selected from H and $C_{1-6}$-alkyl, and wherein the group in each case may optionally be substituted by one or more groups selected from among OH, oxo, halogen, $C_{1-6}$-alkyl and O—$C_{1-6}$-alkyl.

Preferably, this invention relates to a method to prepare the compound of formula 1, wherein $R_A$ is

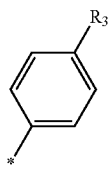

Z denotes a halogen;
X denotes SO;
$R^1$ denotes H or methyl;
$R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$, while $R^{2.1}$ is H or a group selected from among $C_{1-6}$-alkyl, $C_{1-6}$-alkanol, $C_{1-3}$-haloalkyl, mono- or bicyclic $C_{3-10}$ cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl, while $R^{2.2}$ and $R^{2.3}$ independently of one another are H or a group selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$ heterocycle, mono- or bicyclic $C_{5-10}$-heteroaryl, CO—$NH_2$, CO—$NHCH_3$, CO—$N(CH_3)_2$, $SO_2(C_1-C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{5-10}$-cycloalkyl, which may optionally be bridged by one or more $C_{1-3}$-alkyl groups and which may optionally be mono- or polysubstituted by OH or halogen or by one or more groups selected from among branched or unbranched $C_{1-3}$-alkanol, $OR^{2.1}$, $COOR^{2.1}$, $SO_2NR^{2.2}R^{2.3}$, $C_{5-10}$ heterocycle, phenyl, $C_{1-6}$-alkyl, phenyl-$C_{1-6}$-alkylene, $C_{5-6}$-heteroaryl-$C_{1-6}$-alkylene, mono- or bicyclic $C_{5-10}$-cycloalkyl and $NR^{2.2}R^{2.3}$, which may optionally be substituted by one or more groups selected from among OH, $OR^{2.1}$, oxo, halogen, $C_{1-6}$-alkyl, phenyl and $NR^{2.2}R^{2.3}$, or wherein $NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2"}$, $CH_2$—$NR^{2.2}$—CO—$R^{2"}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$ and $NR^{2.2}R^{2.3}$;

$R^3$ denotes fluorine, chlorine, bromine, iodine or CN; and $R^4$ and $R^5$ are independently selected from H and $C_{1-6}$-alkyl.

In another preferred embodiment, this invention relates to a method to prepare the compound of formula 1, wherein $R_A$ is

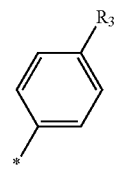

$R^2$ is $C_{1-10}$-alkyl, which may optionally be substituted by one or more groups selected from among $OR^{2.1}$, $COOR^{2.1}$ and $C_{6-10}$-aryl, wherein $R^{2.1}$ is H, or $R^2$ denotes a monocyclic $C_{5-10}$-cycloalkyl, or wherein $NR^1R^2$ together denote a heterocyclic $C_{4-7}$ ring.

In yet another preferred embodiment, this invention relates to a method to prepare the compound of formula 1, wherein $R_A$ is

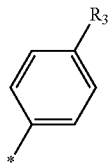

Z denotes chloride;
X denotes SO;
$R^1$ denotes H; and
$R^4$ and $R^5$ are independently H or methyl.

In yet another preferred embodiment, this invention relates to a method to prepare the compound of formula 1, wherein $R_A$ is

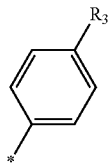

Z denotes chloride;
X denotes SO;
$R^1$ denotes H;
$R^3$ denotes chloride; and
$R^4$ and $R^5$ are independently H or methyl.

In another preferred embodiment, the invention relates to a method to prepare the compound of formula 1, wherein
$R_A$ denotes a monocyclic five- or six-membered heteroaryl ring, which is optionally substituted by a group consisting of
F, Cl, Br, $CF_3$, $CHF_2$, $CH_2F$, CN, OH, -Methyl, Ethyl, Propyl, Isopropyl, —O-Methyl, O-Ethyl, —COOMethyl, —COOEthyl, $SO_2$—$(CH_3)$, SO—$(CH_3)$, $SO_2$—$(CH_2CH_3)$, SO—$(CH_2CH_3)$, Phenyl, -methylene-Phenyl, -ethylene-Phenyl, —$NH_2$, —$NH(CH_3)$, $N(CH_3)_2$, -methylen-$NH_2$, -methylene-$NH(CH_3)$, -methylen-N$(CH_3)_2$, $C_{3-6}$-Cycloalkyl, -methylene-$C_{3-6}$-Cycloalkyl, saturated or partially saturated five- to six-membered heterocyclus, five- to six-membered heteroaryl and -Het, which may optionally be substituted by a residue of the group consisting of OH, F, Cl, Br, $CF_3$, $CHF_2$, $CH_2F$, Methyl, Ethyl, Propyl, Isopropyl, Phenyl, —COO($CH_3$), —O-Methyl and —O-Ethyl.

In yet another preferred embodiment, the invention relates to a method to prepare the compound of formula 1, wherein $R_A$ a bicyclic 9- to 11-membered, saturated, unsaturated or partially saturated heterocyclus, which is optionally substituted by a residue of the group consisting of F, Cl, Br, $CF_3$, $CHF_2$, $CH_2F$, CN, OH, -Methyl, Ethyl, Propyl, Isopropyl, —O-Methyl, O-Ethyl, —COOMethyl, —COOEthyl, $SO_2$—$(CH_3)$, SO—$(CH_3)$, $SO_2$—$(CH_2CH_3)$, SO—$(CH_2CH_3)$, Phenyl, -methylen-Phenyl, -ethylen-Phenyl, —$NH_2$, —$NH(CH_3)$, $N(CH_3)_2$, -methylen-$NH_2$, -methylen-$NH(CH_3)$, -methylen-N$(CH_3)_2$, —$C_{3-6}$-cycloalkyl, -methylene-$C_{3-6}$-cycloalkyl, saturated, partially saturated or unsaturated, five- to six-membered heterocyclus, five- to six-membered heteroaryl, methylene-hetaryl, and -methylene-Het,
which may optionally be substituted by a residue selected from the group consisting of OH, F, Cl, Br, $CF_3$, $CHF_2$, $CH_2F$, Methyl, Ethyl, Propyl, Isopropyl, Phenyl, —COO($CH_3$), —O-Methyl and —O-Ethyl.

In yet another preferred embodiment, the invention relates to a method to prepare the compound of formula 1, wherein $R_A$ is a monocyclic, five- to six-membered heteroaryl ring selected from the group consisting of pyrrol, pyrazole, furane, thiophen, thiazole, imidazole, oxazole, pyridazine, pyrimidine, pyrazine, thiadiazole, oxadiazole, isooxazole, isothiazole and pyridine, which is optionally substituted by a residue selected from the group consisting of F, Cl, Br, $CF_3$, $CHF_2$, $CH_2F$, CN, OH, -Methyl, Ethyl, Propyl, Isopropyl, —O-Methyl, O-Ethyl, —COOMethyl, —COOEthyl, $SO_2$—$(CH_3)$, $SO_2$—$(CH_2CH_3)$, Phenyl, -methylene-Phenyl, -ethylene-Phenyl, —$NH_2$, —$NH(CH_3)$, $N(CH_3)_2$, -methylene-$NH_2$, -methylene-$NH(CH_3)$, -methylene-N$(CH_3)_2$, $C_{3-6}$-cycloalkyl, methylene-$C_{3-6}$-cycloalkyl, Het, Hetaryl, -methylene-Hetaryl, and -methylene-Het, whereas this residue again may optionally be substituted by one or more residues selected from the group consisting of OH, F, Cl, Br, $CF_3$, $CHF_2$, $CH_2F$, Methyl, Ethyl, Propyl, Isopropyl, Phenyl, —COO($CH_3$), —O-Methyl and —O-Ethyl.

In yet another preferred embodiment, the invention relates to a method to prepare the compound of formula 1, wherein $R_A$ is a bicyclic, 9- to 11-membered heterocyclus selected from the group consisting of benzoxazole, benzodioxole, dihydrobenzodioxine, benzodioxine, benzisoxazole, benzothiazole, benzisothiazole, thienopyrimidine, furopyrimidine, thienopyridine, Furopyridine, indole, isoindole, chinoxaline, naphthyridine, pyridopyrazine, pyridopyrimidine, chinoline, isochinoline, benzoimidazole, 6,7,8,9-tetrahydro-5H-pyrazino[2,3-d]azepine, benzothiophene, benzofurane, chinazoline, indazole, isobenzofurane and pteridine, which residue may optionally be substituted by a further residue selected from the group consisting of F, Cl, Br, $CF_3$, $CHF_2$, $CH_2F$, CN, OH, -Methyl, Ethyl, Propyl, Isopropyl, —O-Methyl, O-Ethyl, —COOMethyl, —COOEthyl, $SO_2$—$(CH_3)$, $SO_2$—$(CH_2CH_3)$, Phenyl, -methylene-Phenyl, -ethylene-Phenyl, —$NH_2$, —$NH(CH_3)$, $N(CH_3)_2$, -methylene-$NH_2$, -methylene-$NH(CH_3)$, methylene-$N(CH_3)_2$, $C_{3-6}$-cycloalkyl, methylene-$C_{3-6}$-cycloalkyl, Het, Hetaryl, -methylene-Hetaryl and -methylene-Het,
which residue may optionally again be substituted by a further residue selected from the group consisting of OH, F, Cl, Br, $CF_3$, $CHF_2$, $CH_2F$, Methyl, Ethyl, Propyl, Isopropyl, Phenyl, —COO($CH_3$), —O-Methyl and —O-Ethyl.

The method according to this invention relates to preparing dihydrothienopyrimidine compounds of formula 1:

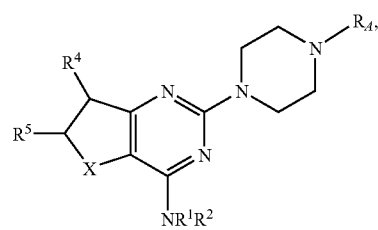

which comprises the steps of:
 a. halogenating, sulfonating or attaching a leaving group to an intermediate of formula 4:

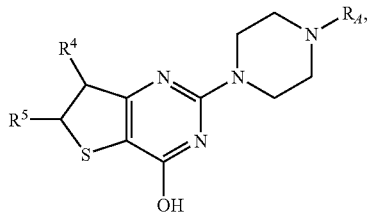

to obtain an intermediate of formula 3:

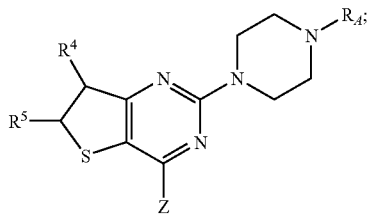

b. stereoselectively oxidizing the intermediate of formula 3 to obtain an intermediate of formula 2:

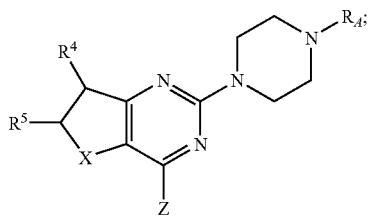

and
 c. reacting the intermediate of formula 2 with a reagent of the formula $HNR^1R^2$ to obtain the compound of formula 1;

wherein Z denotes a halogen, preferably Cl, a sulfonyl or sulfonate leaving group selected from tosylate, mesylate, besylate, brosylate, triflate and nosylate, or a leaving group selected from F, $NO_2$ or $N_2$, $R^1$-$R^5$ and X are as defined herein and the reaction steps are performed without the need for chromatographic purification of intermediates.

Alternatively, the present invention relates to a method of preparing dihydrothieno-pyrimidine compounds of formula 1:

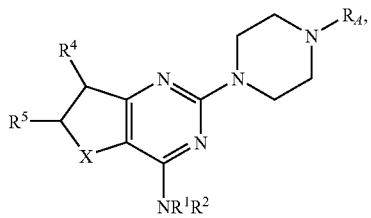

comprising the steps of:
 a. halogenating, sulfonating or attaching a leaving group to an intermediate of formula 4:

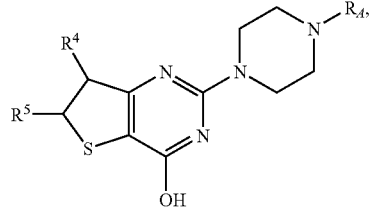

to obtain an intermediate of formula 3:

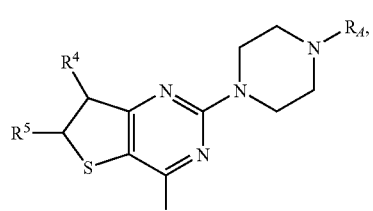

b. reacting the intermediate of formula 3 with a reagent of the formula $HNR^1R^2$ to obtain the compound of formula 8:

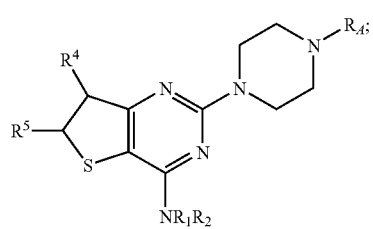

and
 c. stereoselectively oxidizing the intermediate of formula 8 to obtain a compound of formula 1;

wherein $R_A$, $R^1$-$R^5$, Z, Het, Hetaryl, cyclohexyl and X are as defined herein and the reaction steps are performed without the need for chromatographic purification of intermediates by distillation or chromatography.

In a preferred embodiment, the halogenating step (a) is carried out in the presence of $POCl_3$, $SOCl_2$, $SO_2Cl_2$, $(COCl)_2$, $PCl_5$, $POCl_3/PCl_5$, $Cl_2NCS$ in a solvent. Preferably, the solvent is acetonitrile, methylene chloride, toluene or chloroform.

In another preferred embodiment, the oxidation steps (b) or (c) in the above-defined methods are carried out in the presence of a chiral ligand/metal, stoichiometric oxidant and a solvent. Preferably, the chiral ligand/metal Ti/BINOL, substituted BINOL, $WO_3$/chiral ligand, Davis oxaziridine, D-epoxone/oxone, Mn/Salen, Ti/hydrobenzoin variants, Ti/mandelic acid, Ti/DET, V(acac)$_2$ or Fe(acac)$_3$/chiral ligand and the stoichiometric oxidant is cumene hydroperoxide, hydrogen peroxide, t-butyl hydroperoxide solution, MCPBA, peroxybenzoic acids, oxone or dioxiranes. Preferably, the solvent is toluene, methylene chloride, chloroform, acetonitrile, THF or fluorobenzene.

In another preferred embodiment, the reacting steps (c) or (b) in the above-defined methods are carried out in the presence of a base and a solvent. The base is preferably selected from the group consisting of: amines, NaOH, NaH, t-BuONa, t-BuOK, DBU, KN(TMS)$_2$, NaN(TMS)$_2$, LiN(TMS)$_2$, and LDA and the solvent is preferably selected from the group consisting of: THF, diglyme, DMSO, NMP, DMAc, acetonitrile and water.

The invention further relates to intermediates of formula 4:

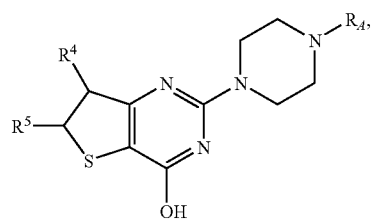

4 wherein $R^3$ is as defined herein, and with the proviso that $R^4$ and $R^5$ cannot both be H.

The invention further relates to intermediates of formula 4:

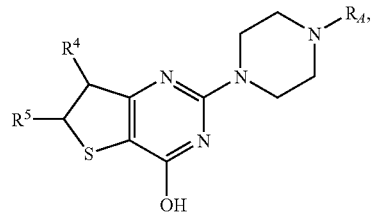

4 wherein $R^3$ is as defined herein, and with the proviso that $R^4$ and $R^5$ are not H.

The invention also relates to the method of preparing intermediates of formula 4, comprising the step of reacting an intermediate of formula 5:

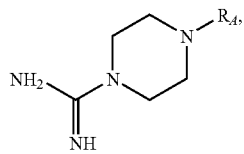

5 with an intermediate of formula 6:

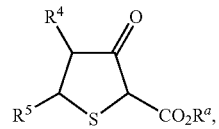

6 in the presence of a base, to obtain the intermediate of formula 4, wherein IV is alkyl, and more preferably methyl, and $R_A$, $R^4$-$R^5$ are as defined herein.

Another aspect of the invention relates to a method for preparing intermediates of formula 4, comprising the step of reacting an intermediate of formula 5:

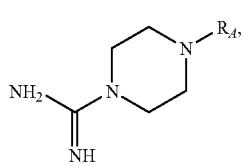

5 with an intermediate of formula 6:

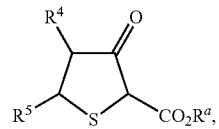

6 in the presence of a base, to obtain the intermediate of formula 4, wherein $R^a$ is alkyl and $R_A$, $R^4$ and $R^5$ are as defined herein. In a preferred embodiment, the base is an alkoxide base or sodium hydride in combination with a solvent, wherein the alkoxide base is preferably t-BuOK, t-BuONa, NaOMe, NaOEt, n-BuLi or t-BuLi and the sodium hydride is in combination with MeOH, NaOH, i-PrOH or t-BuOH.

In a preferred embodiment, $R^4$ and $R^5$ are independently H or methyl. In another preferred embodiment, $R^a$ is methyl. More preferably, $R^4$ and $R^5$ are H and $R^a$ is methyl.

In another aspect, the present invention relates to a practical regioselective synthesis of 3-oxo-tetrahydrothiophene-2-carboxylic acid esters without the formation of undesired regioisomers such as a3 in Equation 1. For example, the invention relates to a method of preparing intermediates of formula 6,

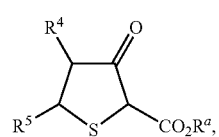

6 comprising the steps of:

a. reacting reagents of the formulas HS—CH$_2$—CO$_2$R$^a$ and CHR$^5$=CR$^4$—CO$_2$R$^a$ to obtain an intermediate of formula 7:

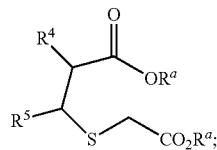

and b. cyclizing the intermediate of formula 7 in a solvent to obtain the intermediate of formula 6, wherein R$^a$, R$^4$-R$^5$ are as defined herein; and wherein the intermediate of formula 6 may be used in a subsequent reaction step without the need for chromatographic purification in that step or optionally, all steps thereafter.

The thioester and α,β-unsaturated ester of the formulas HS—CH$_2$—CO$_2$R$^a$ and CHR$^5$=CR$^4$—CO$_2$R$^a$, respectively, may be reacted under conditions known in the art, e.g., with piperidine, to obtain an intermediate of formula 7.

In preferred embodiments, the reacting step (a) above is performed in the presence of a base and the cyclization step (b) is performed in the presence of TiCl$_4$, TiCl$_2$(OiPr)$_2$, TiCl(OiPr)$_3$, TiCl$_3$(OiPr) or chiral variants thereof, and in the presence of an amine base, such as diisopropyethylamine or triethylamine. In a preferred embodiment, the chiral variant is BINOL, a substituted BINOL, chiral diols, BINAP, DuPhos, Taddols or tartrates.

In yet another preferred embodiment, the cyclization step (b) above is performed in the presence of SnX$_4$, CuX$_2$ or NiX$_2$, wherein X is Cl, Br or OTf, and optionally in the presence of a base. The solvent may be an alcoholic or non-alcoholic solvent, preferably a non-alcoholic solvent. The cyclization step (b) may be carried out at a temperature between 0° C. and −78° C.

In one embodiment of this invention, the compound prepared by the above disclosed methods are:

(R)-2-{(R)-2-[4-(4-Chloro-phenyl)-piperazin-1-yl]-5-oxo-6,7-dihydro-5H-5λ$^4$-thieno[3,2-d]pyrimidin-4-ylamino}-3-methyl-butyric acid methyl ester;

(R)-2-(R)-2-[4-(4-Chloro-phenyl)-piperazin-1-yl]-5-oxo-6,7-dihydro-5H-5λ$^4$-thieno[3,2-d]pyrimidin-4-ylamino-3-methyl-butan-1-ol;

(R)-2-[4-(4-Chloro-phenyl)-piperazin-1-yl]-5-oxo-6,7-dihydro-5H-5λ$^4$-thieno[3,2-d]pyrimidin-4-yl-((S)-1-phenyl-ethyl)-amine;

(R)-2-[4-(4-Chloro-phenyl)-piperazin-1-yl]-5-oxo-6,7-dihydro-5H-5λ$^4$-thieno[3,2-d]pyrimidin-4-yl-cyclohexyl-amine; and (R)-2-[4-(4-Chloro-phenyl)-piperazin-1-yl]-4-piperidin-1-yl-6,7-dihydro-thieno[3,2-d]pyrimidine 5-oxide.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms and Conventions

Unless otherwise stated, all the substituents are independent of one another. If for example there might be a plurality of $C_{1-6}$-alkyl groups as substituents in one group, in the case of three substituents $C_{1-6}$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (I), 4-piperidinyl (II), 2-tolyl (III), 3-tolyl (IV) and 4-tolyl (V) are shown as follows:

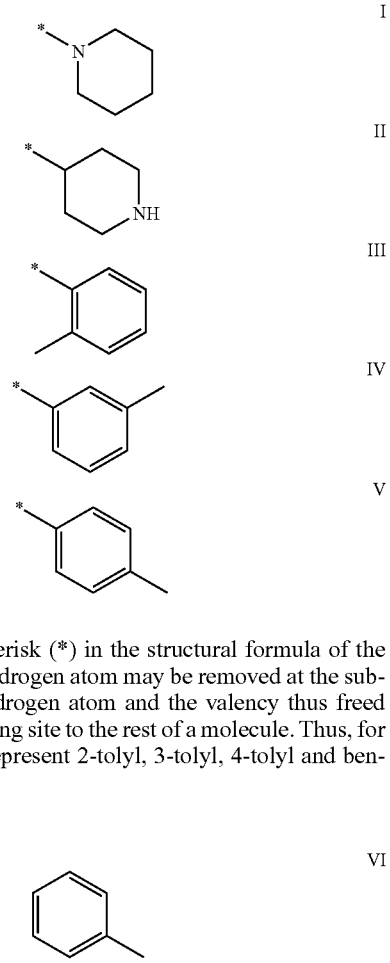

If there is no asterisk (*) in the structural formula of the substituent, each hydrogen atom may be removed at the substituent of each hydrogen atom and the valency thus freed may serve as a binding site to the rest of a molecule. Thus, for example, VI may represent 2-tolyl, 3-tolyl, 4-tolyl and benzyl.

By the term "$C_{1-10}$-alkyl" (including those which are part of other groups) are meant branched and unbranched alkyl groups with 1 to 10 carbon atoms, by the term "$C_{1-6}$-alkyl" are meant accordingly branched and unbranched alkyl groups with 1 to 6 carbon atoms. "$C_{1-4}$-alkyl" accordingly denotes branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neopentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is to be substituted by a group which together with one or two carbon atoms of the alkylene chain forms a carbocyclic ring with 3, 5 or 6 carbon atoms, this includes, inter alia, the following examples of the rings:

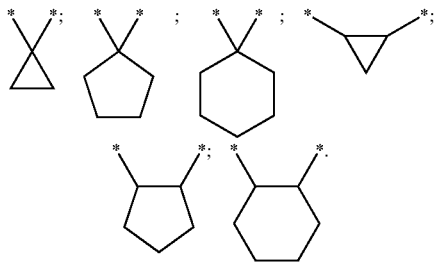

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkynylene groups with 2 to 4 carbon atoms. Alkynylene groups with 2 to 4 carbon atoms are preferred. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 to 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—although already included under "aryl-$C_{1-6}$-alkylene"—branched and unbranched alkylene groups with 1 to 6 carbon atoms, which are substituted by a heteroaryl.

A heteroaryl of this kind includes five or six-membered heterocyclic aromatic groups or 5-10 membered, bicyclic heteroaryl rings which may contain one, two or three heteroatoms, selected from among oxygen, sulphur and nitrogen and sufficient conjugated double bonds to form an aromatic system. The following are examples of five- or six-membered heterocyclic aromatic groups:

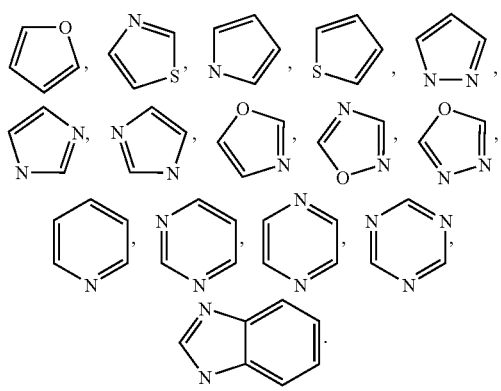

Unless stated otherwise, these heteroaryls may be substituted by one or more groups selected from among methyl, ethyl, iso-propyl, tert-butyl, hydroxy, fluorine, chlorine, bromine and iodine.

The following are examples of the heteroaryl-$C_{1-6}$-alkylenes:

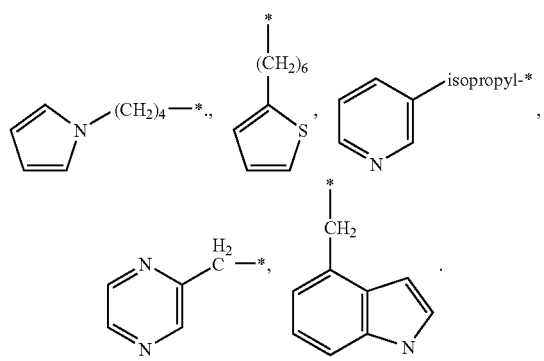

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are meant, in addition, monocyclic alkyl groups with 3 to 7 carbon atoms and also bicyclic alkyl groups with 7 to 10 carbon atoms or also monocyclic alkyl groups which are bridged by at least one $C_{1-3}$-carbon bridge.

By the term "heterocyclic rings" or also "heterocycles" are meant five-, six- or seven-membered, saturated or unsaturated heterocyclic rings which may contain one, two or three heteroatoms, selected from among oxygen, sulphur and nitrogen, while at the same time the ring may be linked to the molecule through a carbon atom or, if available, through a nitrogen atom. Although included under the term "heterocyclic rings" or "heterocycle", the term "heterocyclic non-aromatic rings" defines five-, six- or seven-membered unsaturated rings. Examples include:

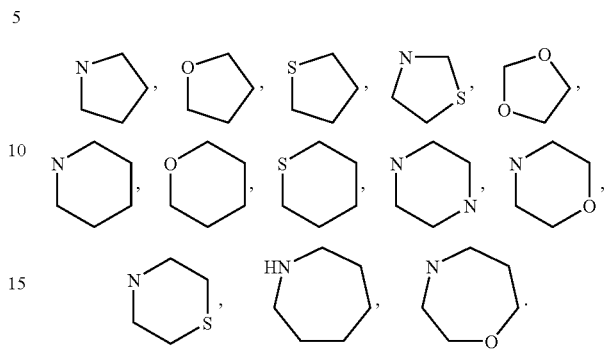

Although included within the term "heterocyclic rings" or "heterocycle", the term "heterocyclic, aromatic rings" or "heteroaryl" defines five- or six-membered heterocyclic aromatic groups or 5-10 membered, bicyclic heteroaryl rings which may contain one, two, three or four heteroatoms, selected from among oxygen, sulphur and nitrogen, and sufficient conjugated double bonds to form an aromatic system. The following are examples of five- or six-membered heterocyclic aromatic groups:

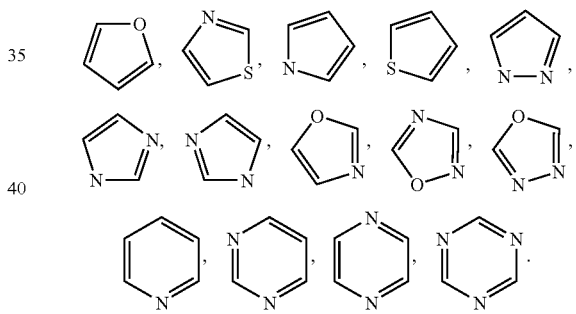

Unless otherwise mentioned, a heterocyclic ring (or "heterocycle") may be provided with a keto group. The following are examples of this.

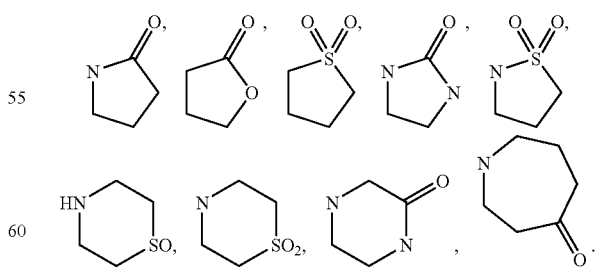

Although already included under "cycloalkyl", the term "bicyclic cycloalkyls" generally denotes eight-, nine- or ten-membered bicyclic carbon rings. The following are mentioned by way of example:

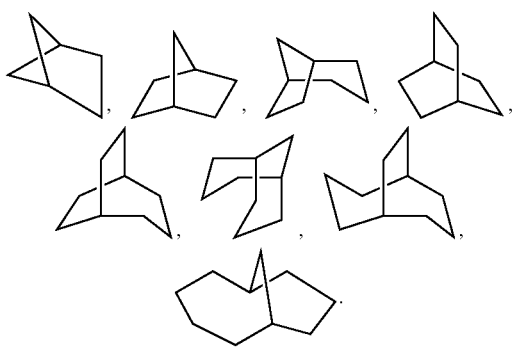

Although already included under "heterocycle", the term "bicyclic heterocycles" generally denotes eight-, nine- or ten-membered bicyclic rings which may contain one or more heteroatoms, preferably 1-4, more preferably 1-3, still more preferably 1-2, particularly one heteroatom, selected from among oxygen, sulphur and nitrogen. At the same time the ring may be linked to the molecule through a carbon atom of the ring or, if available, through a nitrogen atom of the ring. The following are mentioned by way of example:

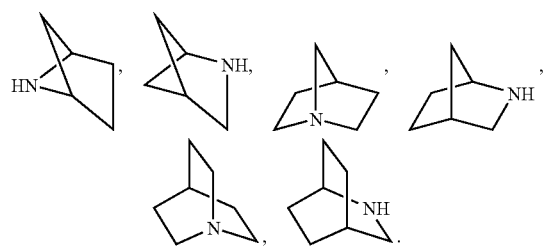

Although already included under "aryl", by a "bicyclic aryl" is meant a 5-10 membered, bicyclic aryl ring which contains sufficient conjugated double bonds to form an aromatic system. One example of a bicyclic aryl is naphthyl.

Although already included under "heteroaryl", by a "bicyclic heteroaryl" is meant a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "condensed cycloalkyl" or "condensed aryl" defines bicyclic rings, wherein the bridge separating the rings denotes a direct single bond. The following are mentioned as examples of a condensed bicyclic cycloalkyl:

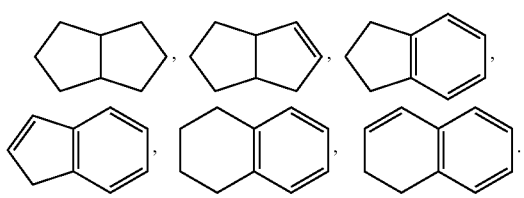

Although included by the term "bicyclic heterocycles" or "bicyclic heteroaryls", the term "condensed, bicyclic heterocycles" or "condensed, bicyclic heteroaryls" defines bicyclic 5-10 membered heterorings which contain one, two or three heteroatoms, selected from among oxygen, sulphur and nitrogen and wherein the bridge separating the rings denotes a direct single bond. The "condensed bicyclic heteroaryls" also contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

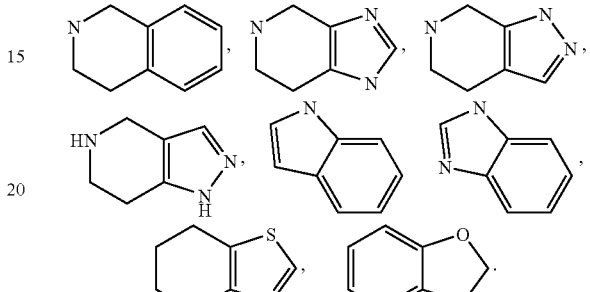

By the term "heterocyclic Spiro rings" (Spiro) are meant 5-10 membered, spirocyclic rings which may optionally contain one, two or three heteroatoms, selected from among oxygen, sulphur and nitrogen, while at the same time the ring may be linked to the molecule through a carbon atom or if available through a nitrogen atom. Unless otherwise mentioned, a spirocyclic ring may be provided with an oxo, methyl or ethyl group. Examples of this include:

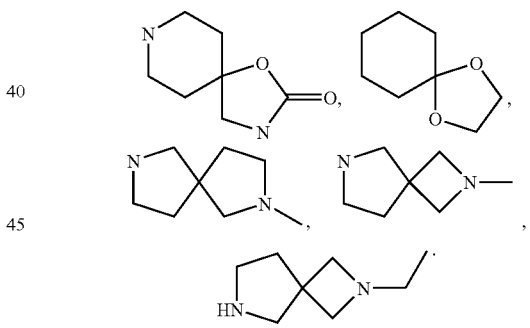

"Halogen" or "halo" within the scope of the present invention denotes fluorine, chlorine, bromine or iodine. Unless stated to the contrary, fluorine, chlorine and bromine are regarded as preferred halogens.

Compounds of general formula 1 prepared by the method of the present invention may have acid groups, chiefly carboxyl groups, and/or basic groups such as e.g. amino functions. Compounds of general formula 1 may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alklaline earth metal hydroxides or carbonates, zinc or ammonium hydroxides or organic amines such as e.g. diethylamine, triethylamine, triethanolamine inter alia.

B. Salts, Diastereomers, Enantiomers, Racemates, Hydrates and Solvates

The compounds of formula 1 and equivalent expressions are meant to embrace compounds of formula 1, either individually, in some combination, or all of them, as the context permits. As defined herein, the compounds of formula 1 include the pharmaceutically acceptable salts, diastereomers, enantiomers, racemates, hydrates or solvates thereof.

As mentioned hereinbefore, the compounds of formula 1 prepared by the method of the present invention may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula 1 with inorganic or organic acids. On the other hand, if R is hydrogen, the compound of formula 1 prepared by the method of the present invention may also be converted by a further reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula 1 are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred. The compounds of the present invention are useful in both free base and salt form and in practice, the use of the salt form amounts to use of the base form. Lists of suitable salts are found in, e.g., S. M. Birge et al., *J. Pharm. Sci.*, 1977, 66, 1-19, which is hereby incorporated by reference in its entirety.

If desired, the compounds of general formula 1 prepared by the method of the present invention may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds prepared by the method of the present invention, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid. The term "enantiomers" means a pair of stereoisomers that are non-superimposable mirror images of each other. The terms "diastereoisomers" or "diastereomers" mean optical isomers which are not mirror images of each other. The terms "racemic mixture" or "racemate" mean a mixture containing equal parts of individual enantiomers. The term "non-racemic mixture" means a mixture containing unequal parts of individual enantiomers.

The compounds prepared by the method of the present invention may optionally occur as racemates, but they may also be obtained as pure enantiomers, i.e. in the (R) or (S) form. In one embodiment, the compounds prepared by the present method are those which occur as racemates or as the (S) form. In another embodiment the compounds prepared by the present method are the (R) form.

The invention relates to the compounds prepared by the method of the present invention, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The term "solvate" means a physical association of a compound with one or more solvent molecules or a complex of variable stoichiometry formed by a solute (for example, a compound of formula 1) and a solvent, for example, water, ethanol, or acetic acid. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

Representative Dihydrothienopyrimidine Compounds

The present invention relates to synthetic steps to prepare dihydrothienopyrimidine compounds of formula 1:

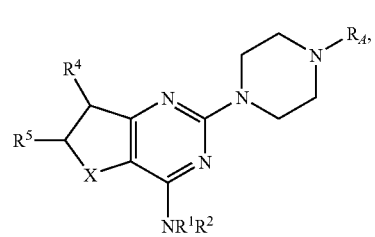

wherein:

$R_A$ denotes a residue selected from among the group consisting of Het, Hetaryl and, which is optionally substituted by a residue selected from the group consisting of halogen, $C_{1-3}$-fluoroalkyl, CN, OH, Oxo, —$C_{1-6}$-Alkyl, —COOR$^{2.1}$, SO—R$^{2.1}$, SO$_2$—R$^{2.1}$, $C_{6-10}$-Aryl, $C_{1-3}$-alkylene-$C_{6-10}$-Aryl, —$C_{1-3}$-alkylene-NR$^{2.2}$R$^{2.3}$, —NR$^{2.2}$R$^{2.3}$, $C_{3-10}$-cycloalkyl, $C_{1-3}$-alkylen-$C_{3-10}$-cycloalkyl, Het, Hetaryl, $C_{1-3}$-alkylen-Hetaryl, and $C_{1-3}$-alkylen-Het, which may optionally be substituted by a residue selected form among OH, Halogen, —$C_{1-3}$-Fluoroalkyl, $C_{1-6}$-Alkyl, $C_{6-10}$-Aryl, —COO($C_{1-3}$-Alkyl) and O—($C_{1-3}$-Alkyl), with Het being a three- to eleven-membered, mono- or bicyclic, saturated or partially saturated heterocyclus which contains 1, 2, 3 or 4 heteroatoms which are independently selected from among N, S or O, Hetaryl being a five- to eleven-membered, mono- or bicyclic heteroaryl which contains 1, 2, 3 or 4 heteroatoms which are independently selected from among N, S or O,
with
cycloalkyl being saturated or partially saturated,
or wherein
$R_4$ denotes

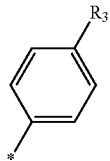

and wherein
X denotes SO or $SO_2$, preferably SO;
$R^1$ denotes H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene or $C_{5-10}$-heteroaryl-$C_{1-6}$-alkylene;
$R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$,
while $R^{2.1}$ is H or a group selected from among $C_{1-6}$-alkyl, $C_{1-6}$-alkanol, $C_{1-3}$-haloalkyl, mono- or bicyclic $C_{3-10}$ cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl, while $R^{2.2}$ and $R^{2.3}$ independently of one another are H or a group selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$ heterocycle, mono- or bicyclic $C_{5-10}$-heteroaryl, CO—$NH_2$, CO—$NHCH_3$, CO—$N(CH_3)_2$, $SO_2(C_1$-$C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$,
or
$R^2$ denotes a mono- or polycyclic $C_{3-10}$ cycloalkyl, which may optionally be bridged by one or more $C_{1-3}$-alkyl groups and which may optionally be substituted by a group selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$,
or
$R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1-6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$,
or
$R^2$ denotes a group selected from among mono- or bicyclic, saturated or unsaturated $C_{3-10}$ heterocycle and a mono- or bicyclic $C_{5-10}$-heteroaryl, which includes 1 to 4 heteroatoms selected from among S, O and N and optionally by one or more groups selected from among halogen, OH, oxo and SH or by one or more groups selected from among $OR^{2.1}$, $SR^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl, $CH_2$—$NR^{2.2}R^{2.3}$ and $NR^{2.2}R^{2.3}$;
or wherein,
$NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—CH—$NR^{2.2}R^{2.3}$, $CH_2$—$NR^{2.2}SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$ and $NR^{2.2}R^{2.3}$;
$R^3$ is selected from among fluorine, chlorine, bromine, iodine, hydroxy, $SO_2$—$CH_3$, $COOR^{2.1}$, nitrile group and $C_{3-10}$ heterocycle-$C_{1-6}$-alkylene, wherein the $C_{3-10}$ heterocycle may be mono- or bicyclic and may optionally be substituted by a group selected from among OH, halogen, oxo, $C_{1-6}$-alkyl and $C_{6-10}$-aryl,
or
is a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-hetero aryl-$C_{1-6}$-alkylene, $C_{3-10}$ heterocycle and $C_{3-10}$-cycloalkyl, which may optionally be substituted by a group selected from among OH, halogen, oxo, $C_{1-6}$-alkyl and $C_{6-10}$-aryl,
or
$R^3$ denotes the group —CO—$NR^{3.1}R^{3.2}$,
wherein $R^{3.1}$ and $R^{3.2}$ independently of one another are H or groups selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{3-10}$ heterocycle, $C_{3-10}$ heterocycle-$C_{1-6}$-alkylene and mono- or bicyclic $C_{5-10}$-heteroaryl, wherein the group in each case may optionally be substituted by one or more groups selected from among OH, oxo, halogen, $C_{1-6}$-alkyl and O—$C_{1-6}$-alkyl,
or
$R^3$ denotes the group —$NR^{3.3}$—CO—$R^{3.4}$,
wherein $R^{3.3}$ is H or a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{3-10}$ heterocycle and a $C_{5-10}$-heteroaryl, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, and wherein $R^{3.4}$ is H or a group selected from among $C_{1-6}$-alkyl, $C_{2-6}$-alkenyl, $C_{2-6}$- alkynyl, $C_{1-6}$-alkanol, $OR^{2.1}$, $CH_2$—O—CO—$C_{1-6}$-alkyl, $CH_2$—$NR^{2.2}R^{2.3}$, $NR^{2.2}R^{2.3}$, $C_{6-10}$-aryl; $C_{6-10}$-aryl-$C_{1-6}$-alkylene, $C_{5-10}$-heteroaryl-$C_{1-6}$-alkylene, mono- or bicyclic, saturated, partially saturated or unsaturated $C_{3-10}$ heterocycle with 1, 2 or 3 heteroatoms selected from among S, O and N and a mono- or bicyclic $C_{5-10}$-heteroaryl with 1, 2 or 3 heteroatoms selected from among S, O and N, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, or $R^3$ denotes an optionally mono- or di-N-substituted sulphonamide group $SO_2$—$NR^{3.5}R^{3.6}$, wherein $R^{3.5}$ and $R^{3.6}$ may each independently of one another be $C_{1-6}$-alkyl or $C_{6-10}$-aryl;

and $R^4$ and $R^5$ are independently selected from H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{5-10}$-heteroaryl-$C_{1-6}$-alkylene, $C_{3-10}$ heterocycle and a $C_{5-10}$-heteroaryl, —O—$C_{1-6}$-alkyl, —O—$C_{6-10}$-aryl, —O—$C_{3-10}$ heterocycle and —O—$C_{5-10}$-heteroaryl, —NR'R", fluoro, $C_{1-6}$-fluoroalkyl, and $C_{1-6}$-fluoroalkoxy, wherein R' and R" are independently selected from H and $C_{1-6}$-alkyl, and wherein the group in each case may optionally be substituted by one or more groups selected from among OH, oxo, halogen, $C_{1-6}$-alkyl and O—$C_{1-6}$-alkyl, as well as pharmacologically acceptable salts, diastereomers, enantiomers, racemates, hydrates or solvates thereof.

The invention preferably relates to the method of preparing compounds of formula 1, wherein:

X denotes SO;

$R^1$ denotes H, $C_{1-6}$-alkyl, $C_{6-10}$-aryl, $C_{6-10}$-aryl-$C_{1-6}$-alkylene or $C_{5-10}$-heteroaryl-$C_{1-6}$-alkylene;

$R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{3-10}$-cycloalkyl, a $C_{6-10}$-aryl-$C_{1-6}$-alkylene or $C_{5-10}$-heteroaryl-$C_{1-6}$-alkylene, $C_{3-10}$ heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated $C_{3-10}$ heterocycle, which may optionally be substituted by one or more groups selected from among OH, halogen, $C_{1-6}$-alkyl, $C_{6-10}$-aryl, wherein $R^{2.2}$ and $R^{2.3}$ independently of one another are H or are selected from among halogen, $C_{1-6}$ alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic, saturated or unsaturated $C_{3-10}$ heterocycle, mono- or bicyclic $C_{5-10}$-heteroaryl, CO—$NH_2$, CO—$NHCH_3$, CO—N($CH_3$)$_9$, $SO_2(C_1$-$C_2$-alkyl), CO—$R^2$ and $COOR^{2.1}$, which may optionally be substituted by one or more groups selected from among OH, halogen, $C_{1-6}$-alkyl, $C_{6-10}$-aryl and $COOR^{2.1}$, or $R^2$ denotes a mono- or polycyclic $C_{3-10}$-cycloalkyl, which may optionally be bridged by one or more $C_{1-3}$-alkyl groups and which may optionally be mono- or polysubstituted by OH or halogen or by one or more groups selected from among branched or unbranched $C_{1-6}$-alkanol, $OR^{2.1}$, $COOR^{2.1}$, $SO_2NR^{2.2}R^{2.3}$, $C_{3-10}$ heterocycle, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, mono- or bicyclic $C_{3-10}$-cycloalkyl and $NR^{2.2}R^{2.3}$, which may optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, $C_{3-10}$ heterocycle, $C_{1-6}$-alkyl, $C_{6-10}$-aryl-$C_{1\_6}$-alkylene, $C_{3-10}$ heterocycle-$C_{1-6}$-alkylene, $C_{5-10}$-heteroaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $R^2$ denotes a group selected from among mono or bicyclic, saturated or unsaturated $C_{3-10}$ heterocycle and a mono- or bicyclic $C_{5-10}$-heteroaryl, which includes 1 to 4 heteroatoms selected from among S, O and N and may optionally be substituted by one or more groups selected from among halogen, OH, oxo and SH or by one or more groups selected from among $OR^{2.1}$, $SR^{2.1}COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, $C_{5-10}$-heteroaryl-$C_{1-6}$-alkylene, $C_{5-10}$ heterocycle, $C_{5-10}$-heteroaryl, $C_{1-6}$-alkanol and $NR^{2.2}R^{2.3}$, which may in turn optionally be substituted by one or more groups selected from among OH, $OR^{2.1}$, oxo, halogen, $C_{1-6}$-alkyl, $C_{6-10}$-aryl and $NR^{2.2}R^{2.3}$, or $NR^1R^2$ together denotes a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$R^{2.2}$—CO—$CH_2$—$R^{2.2}R^{2.3}$, $CH_2$—$NR^{2.2}$—$SO_2$—$C_{1-3}$-alkyl, $CH_2NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$; and $R^4$ and $R^5$ are independently selected from H, $C_{1-6}$-alkyl, $C_{6-10}$-aryl, —O—$C_{1-6}$-alkyl, —NR'R", fluoro, $C_{1-6}$-fluoroalkyl, and $C_{1-6}$-fluoroalkoxy, wherein R' and R" are independently selected from H and $C_{1-6}$-alkyl, as well as pharmacologically acceptable salts, diastereomers, enantiomers, racemates, hydrates or solvates thereof.

Also preferred is the method of preparing compounds of formula 1, wherein:

X denotes SO;

$R^1$ denotes H, $C_{1-6}$-alkyl, $C_{6-10}$-aryl, $C_{6-10}$-aryl-$C_{1-6}$-alkylene or $C_{5-10}$-heteroaryl-$C_{1-6}$-alkylene;

$R^2$ is H or $C_{1-6}$-alkyl, which may optionally be substituted by halogen and which may optionally be substituted by one or more groups selected from among $OR^{2.1}$, $COOR^{2.1}$, $CONR^{2.2}R^{2.3}$, $SR^{2.1}$, phenyl, a mono- or bicyclic $C_{5-10}$ heterocycle, $C_{5-6}$-heteroaryl, a mono- or bicyclic $C_{5-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, phenyl, $COOR^{2.1}$, $CH_2$—$NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, a mono- or bicyclic $C_{5-10}$ cycloalkyl, a phenyl-$C_{1-6}$-alkylene, a $C_{5-6}$-heteroaryl-$C_{1-6}$-alkylene, $C_{5-10}$-heterocycle-$C_{1-6}$-alkylene, $C_{5-10}$-cycloalkyl-$C_{1-6}$-alkylene, phenyl, a mono- or bicyclic $C_{5-10}$-heteroaryl and a mono- or bicyclic, saturated or unsaturated $C_{5-10}$ heterocycle, which may optionally be substituted by one or more groups selected from among OH, halogen, $C_{1-6}$-alkyl and phenyl, wherein $R^{2.2}$ and $R^{2.3}$ independently of one another are H or a group selected from among halogen, $C_{1-6}$-alkyl, mono- or bicyclic $C_{5-10}$ cycloalkyl, phenyl-$C_{1-6}$-alkylene, $C_{5-6}$-heteroaryl-$C_{1-6}$-alkylene, phenyl, mono or bicyclic $C_{5-10}$ heterocycle, mono- or bicyclic $C_{5-6}$-heteroaryl, CO—NH), CO—NHCH$_3$, CO—N(CH$_3$)$_2$, SO$_2$ (C$_1$-C$_2$-alkyl), CO—$R^{2.1}$ and COOR$^{2.1}$, which may optionally be substituted by one or more groups selected from among OH, halogen, $C_{1-6}$-alkyl, phenyl and COOR$^{2.1}$, or $R^2$ denotes a mono- or polycyclic $C_{5-10}$-cycloalkyl, which may optionally be bridged by one or more $C_{1-3}$-alkyl groups and which may optionally be mono- or polysubstituted by OH or halogen or by one or more groups selected from among branched or unbranched $C_{1-3}$-alkanol, OR$^{2.1}$, COOR$^{2.1}$, SO$_2$NR$^{2.2}$R$^{2.3}$, $C_{5-10}$ heterocycle, phenyl, $C_{1-6}$-alkyl, phenyl-$C_{1-6}$-alkylene, $C_{5-6}$-heteroaryl-$C_{1-6}$-alkylene, mono- or bicyclic $C_{5-10}$-cycloalkyl and NR$^{2.2}$R$^{2.3}$, which may optionally be substituted by one or more groups selected from among OH, OR$^{2.1}$, oxo, halogen, $C_{1-6}$-alkyl, phenyl and NR$^{2.2}$R$^{2.3}$, or $R^2$ denotes a phenyl, which may optionally be substituted by OH, SH or halogen or by one or more groups selected from among OR$^{2.1}$, COOR$^{2.1}$, NR$^{2.2}$R$^{2.3}$, CH$_2$—NR$^{2.2}$R$^{2.3}$, $C_{5-10}$-cycloalkyl, $C_{5-10}$ heterocycle, $C_{1-6}$-alkyl, phenyl-$C_{1-6}$-alkylene, $C_{5-10}$ heterocycle-$C_{1-6}$-alkylene, $C_{5-6}$-heteroaryl-$C_{1-6}$-alkylene, phenyl, SO$_2$—CH$_3$, SO$_2$—CH$_2$CH$_3$ and SO$_2$—NR$^{2.2}$R$^{2.3}$, which may in turn optionally be substituted by one or more groups selected from among OH, OR$^{2.1}$, oxo, halogen, $C_{1-6}$-alkyl, $C_{6-10}$-aryl and NR$^{2.2}$R$^{2.3}$, or $R^2$ denotes a group selected from among mono or bicyclic, saturated or unsaturated $C_{5-10}$ heterocycle and mono- or bicyclic $C_{5-6}$-heteroaryl, which contains 1 to 4 heteroatoms selected from among S, O and N and may optionally be substituted by one or more groups selected from halogen, OH, oxo and SH or by one or more groups selected from among OR$^{2.1}$, SR$^{2.1}$, COOR$^{2.1}$, COR$^{2.1}$, $C_{1-6}$-alkanol, $C_{3-10}$-cycloalkyl, phenyl, $C_{1-6}$-alkyl, phenyl-$C_{1-6}$-alkylene, $C_{5-6}$-heteroaryl-$C_{1-6}$-alkylene, $C_{5-10}$ heterocycle, $C_{5-6}$-heteroaryl, $C_{1-6}$-alkanol and NR$^{2.2}$R$^{2.3}$, which may in turn optionally be substituted by one or more groups selected from among OH, OR$^{2.1}$, oxo, halogen, $C_{1-6}$-alkyl, phenyl and NR$^{2.2}$R$^{2.3}$; and $R^4$ and $R^5$ are independently selected from H, $C_{6-10}$-aryl, —NR'R'', fluoro, $C_{1-6}$-fluoroalkyl, and $C_{1-6}$-fluoroalkoxy, wherein R' and R'' are independently selected from H and $C_{1-6}$-alkyl, as well as pharmacologically acceptable salts, diastereomers, enantiomers, racemates, hydrates or solvates thereof.

Also particularly preferred is the method of preparing compounds of formula 1, wherein:

NR$^1$R$^2$ together denotes a heterocyclic $C_{4-7}$ ring, which may optionally be bridged, which contains 1, 2 or 3 heteroatoms selected from among N, O and S and which may optionally be substituted by one or more groups selected from among OH, OR$^{2.1}$, $C_{1-6}$-alkanol, oxo, halogen, $C_{1-6}$-alkyl, $C_{6-10}$-aryl, COOR$^{2.1}$, CH$_2$—NR$^{2.2}$—COO—R$^{2.1}$, CH$_2$—NR$^{2.2}$—CO—R$^{2.1}$, CH$_2$—NR$^{2.2}$—CO—CH$_2$—NR$^{2.2}$R$^{2.3}$, CH$_2$—NR$^{2.2}$SO$_2$—$C_{1-3}$-alkyl, CH$_2$—NR$^{2.2}$—CO—NR$^{2.2}$R$^{2.3}$, CO—NR$^{2.2}$R$^{2.3}$, CH$_2$—NR$^{2.2}$R$^{2.3}$ and NR$^{2.2}$R$^{2.3}$, as well as pharmacologically acceptable salts, diastereomers, enantiomers, racemates, hydrates or solvates thereof.

The invention preferably relates to the method of preparing compounds according to formula 1, wherein $R_A$ is

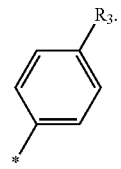

Also preferred is a method of preparing compounds according to formula 1, wherein $R_A$ denotes a monocyclic five- or six-membered heteroaryl ring, which is optionally substituted by a group consisting of F, Cl, Br, CF$_3$, CHF$_2$, CH$_2$F, CN, OH, -Methyl, Ethyl, Propyl, Isopropyl, —O-Methyl, O-Ethyl, —COOMethyl, —COOEthyl, SO$_2$—(CH$_3$), SO—(CH$_3$), SO$_2$—(CH$_2$CH$_3$), SO—(CH$_2$CH$_3$), Phenyl, -methylene-Phenyl, -ethylene-Phenyl, —NH$_2$, —NH(CH$_3$), N(CH$_3$)$_2$, -methylen-NH$_2$, -methylene-NH(CH$_3$), -methylen-N(CH$_3$)$_2$, $C_{3-6}$-Cycloalkyl, -methylene-$C_{3-6}$-Cycloalkyl, saturated or partially saturated five- to six-membered heterocyclus, five- to six-membered heteroaryl and -Het, which may optionally be substituted by a residue of the group consisting of OH, F, Cl, Br, CF$_3$, CHF$_2$, CH$_2$F, Methyl, Ethyl, Propyl, Isopropyl, Phenyl, —COO(CH$_3$), —O-Methyl and —O-Ethyl;

or $R_A$ a bicyclic 9- to 11-membered, saturated, unsaturated or partially saturated heterocyclus, which is optionally substituted by a residue of the group consisting of F, Cl, Br, CF$_3$, CHF$_2$, CH$_2$F, CN, OH, -Methyl, Ethyl, Propyl, Isopropyl, —O-Methyl, O-Ethyl, —COOMethyl, —COOEthyl, SO$_2$—(CH$_3$), SO—(CH$_3$), SO$_2$—(CH$_2$CH$_3$), SO—(CH$_2$CH$_3$), Phenyl, -methylen-Phenyl, -ethylen-Phenyl, —NH$_2$, —NH(CH$_3$), N(CH$_3$)$_2$, -methylene-NH$_2$, -methylen-NH(CH$_3$), -methylen-N(CH$_3$)$_2$, —$C_{3-6}$-cycloalkyl, -methylene-$C_{3-6}$-cycloalkyl, saturated, partially saturated or unsaturated, five- to six-membered heterocyclus, five- to six-membered heteroaryl, methylene-hetaryl, and -methylene-Het, which may optionally be substituted by a residue selected from the group consisting of OH, F, Cl, Br, CF$_3$, CHF$_2$, CH$_2$F, Methyl, Ethyl, Propyl, Isopropyl, Phenyl, —COO(CH$_3$), —O-Methyl and —O-Ethyl;

or $R_A$ is a monocyclic, five- to six-membered heteroaryl ring selected from the group consisting of pyrrol, pyrazole, furan, thiophen, thiazole, imidazole, oxazole, pyridazine, pyrimidine, pyrazine, thiadiazole, oxadiazole, isooxazole, isothiazole and pyridine, which is optionally substituted by a residue selected from the group consisting of F, Cl, Br, CF$_3$, CHF$_2$, CH$_2$F, CN, OH, -Methyl, Ethyl, Propyl, Isopropyl, —O-Methyl, O-Ethyl, —COOMethyl, —COOEthyl, SO$_2$—(CH$_3$), SO$_2$—(CH$_2$CH$_3$), Phenyl, -methylene-Phenyl, -ethylene-Phenyl, —NH$_2$, —NH(CH$_3$), N(CH$_3$)$_2$, -methylene-NH$_2$, -methylene-NH(CH$_3$), -methylene-N(CH$_3$)$_2$, C$_{3-6}$-cycloalkyl, methylene-C$_{3-6}$-cycloalkyl, Het, Hetaryl, -methylene-Hetaryl, and -methylene-Het, whereas this residue again may optionally be substituted by one or more residues selected from the group consisting of OH, F, Cl, Br, CF$_3$, CHF$_2$, CH$_2$F, Methyl, Ethyl, Propyl, Isopropyl, Phenyl, —COO(CH$_3$), —O-Methyl and —O-Ethyl; or R$_A$ is a bicyclic, 9- to 11-membered heterocyclus selected from the group consisting of benzoxazole, benzodioxole, dihydrobenzodioxine, benzodioxine, benzisoxazole, benzothiazole, benzisothiazole, thienopyrimidine, furopyrimidine, thienopyridine, Furopyridine, indole, isoindole, chinoxaline, naphthyridine, pyridopyrazine, pyridopyrimidine, chinoline, isochinoline, benzoimidazole, 6,7,8,9-tetrahydro-5H-pyrazino[2,3-d]azepine, benzothiophene, benzofurane, chinazoline, indazole, isobenzofurane and pteridine, which residue may optionally be substituted by a further residue selected from the group consisting of F, Cl, Br, CF$_3$, CHF$_2$, CH$_2$F, CN, OH, -Methyl, Ethyl, Propyl, Isopropyl, —O-Methyl, O-Ethyl, —COOMethyl, —COOEthyl, SO$_2$—(CH$_3$), SO$_2$—(CH$_2$CH$_3$), Phenyl, -methylene-Phenyl, -ethylene-Phenyl, —NH$_2$, —NH(CH$_3$), N(CH$_3$)$_2$, -methylene-NH$_2$, -methylene-NH(CH$_3$), -methylene-N(CH$_3$)$_2$, C$_{3-6}$-cycloalkyl, methylene-C$_{3-6}$-cycloalkyl, Het, Hetaryl, -methylene-Hetaryl and -methylene-Het, which residue may optionally again be substituted by a further residue selected from the group consisting of OH, F, Cl, Br, CF$_3$, CHF$_2$, CH$_2$F, Methyl, Ethyl, Propyl, Isopropyl, Phenyl, —COO(CH$_3$), —O-Methyl and —O-Ethyl.

The invention preferably also relates to the method of preparing compounds according to formula 1, wherein R$^1$ is H or methyl, as well as pharmacologically acceptable salts, diastereomers, enantiomers, racemates, hydrates or solvates thereof.

The invention preferably also relates to the method of preparing compounds according to formula 1, wherein R$^4$ and R$^5$ are H or methyl, as well as pharmacologically acceptable salts, diastereomers, enantiomers, racemates, hydrates or solvates thereof.

The invention preferably also relates to the method of preparing compounds according to formula 1, wherein R$^4$ and R$^5$ are H, as well as pharmacologically acceptable salts, diastereomers, enantiomers, racemates, hydrates or solvates thereof.

The invention preferably also relates to the method of preparing compounds according to formula 1, wherein:
NR$^1$R$^2$ together form a pyrrolidine ring, which may optionally be substituted by one or more groups selected from among OH, OR$^{2.1}$, CH$_2$—OH, CH$_2$—CH$_2$—OH, oxo, Cl, F, Br, methyl, ethyl, propyl, phenyl, COOR$^{2.1}$, CH$_2$—NR$^{2.2}$—COO—R$^{2.1}$, CH$_2$—NR$^{2.2}$—CO—R$^{2.1}$, CH$_2$—NR$^{2.2}$—CO—CH$_2$—NR$^{2.2}$R$^{2.3}$, CH$_2$—NR$^{2.2}$—SO$_2$—C$_{1-3}$-alkyl, CH$_2$—NR$^{2.2}$ SO$_2$NR$^{2.2}$R$^{2.3}$, CH$_2$—NR$^{2.2}$—CO—NR$^{2.2}$R$^{2.3}$, CO—NR$^{2.2}$R$^{2.3}$, and NR$^{2.2}$R$^{2.3}$,
as well as pharmacologically acceptable salts, diastereomers, enantiomers, racemates, hydrates or solvates thereof.

The invention preferably also relates to the method of preparing compounds according to formula 1, wherein:
R$^2$ denotes phenyl, which is mono- or polysubstituted by OH, SH or halogen and/or by one or more groups selected from among OR$^{2.1}$, COOR$^{2.1}$, NR$^{2.2}$R$^{2.3}$, CH$_2$—NR$^{2.2}$R$^{2.3}$, C$_{5-10}$-cycloalkyl, C$_{5-10}$ heterocycle, C$_{1-6}$-alkyl, phenyl-C$_{1-6}$-alkylene, C$_{5-10}$ heterocycle-C$_{1-6}$-alkylene, C$_{5-6}$-heteroaryl-C$_{1-6}$-alkylene, phenyl, SO$_2$—CH$_3$, SO$_2$—CH$_2$CH$_3$ and SO$_2$—NR$^{2.2}$R$^{2.3}$ at any position, which may in turn optionally be substituted by one or more groups selected from among OH, OR$^{2.1}$, oxo, halogen, C$_{1-6}$-alkyl, phenyl and NR$^{2.2}$R$^{2.3}$,
as well as pharmacologically acceptable salts, diastereomers, enantiomers, racemates, hydrates or solvates thereof.

The invention preferably also relates to the method of preparing compounds according to formula 1, wherein:
R$^2$ is phenyl, which may be substituted in at least one of the two meta positions by OH, SH or halogen or by one or more groups selected from among OR$^{2.1}$, COOR$^{2.1}$, NR$^{2.2}$R$^{2.3}$, CH$_2$—NR$^{2.2}$R$^{2.3}$, C$_{5-10}$-cycloalkyl, C$_{5-10}$ heterocycle, C$_{1-6}$-alkyl, phenyl-C$_{1-6}$-alkylene, C$_{5-10}$ heterocycle-C$_{1-6}$-alkylene, C$_{5-6}$-heteroaryl-C$_{1-6}$-alkylene, phenyl SO$_2$—CH$_3$, SO$_2$—CH$_2$CH$_3$ and SO$_2$—NR$^{2.2}$R$^{2.3}$, which may in turn optionally be substituted by one or more groups selected from among OH, OR$^{2.1}$, oxo, halogen, C$_{1-6}$-alkyl, phenyl and NR$^{2.2}$R$^{2.3}$,
as well as pharmacologically acceptable salts, diastereomers, enantiomers, racemates, hydrates or solvates thereof.

The invention preferably also relates to the method of preparing compounds according to formula 1, wherein:
R$^2$ is phenyl, which is substituted in at least one of the two meta positions by one or more groups selected from among methyl, F, Cl, OH, OR$^{2.1}$, COOR$^{2.1}$, NH$_2$ and N(CH$_3$)$_2$,
as well as pharmacologically acceptable salts, diastereomers, enantiomers, racemates, hydrates or solvates thereof.

The invention preferably also relates to the above method of preparing compounds according to formula 1, wherein:
R$^2$ is C$_{1-6}$-alkyl, which may optionally be substituted by halogen and which may optionally be substituted by one or more groups selected from among OR$^{2.1}$, COOR$^{2.1}$, CONR$^{2.2}$R$^{2.3}$, SR$^{2.1}$, phenyl, a mono- or bicyclic C$_{5-10}$ heterocycle, C$_{5-6}$-heteroaryl, a mono- or bicyclic C$_{5-10}$-cycloalkyl, CH—NR$^{2.2}$R$^{2.3}$ and NR$^{2.2}$R$^{2.3}$, which in turn may be substituted by one or more groups selected from among OH, halogen, OR$^{2.1}$, oxo, C$_{1-6}$-alkyl, phenyl, COOR$^{2.1}$, CH$_2$—NR$^{2.2}$R$^{2.3}$ and NR$^{2.2}$R$^{2.3}$,
as well as pharmacologically acceptable salts, diastereomers, enantiomers, racemates, hydrates or solvates thereof.

The invention preferably also relates to the above method of preparing compounds according to formula 1, wherein:
R$^2$ is methyl, ethyl or propyl,
as well as pharmacologically acceptable salts, diastereomers, enantiomers, racemates, hydrates or solvates thereof.

The invention preferably also relates to the above method of preparing compounds according to formula 1, wherein:
R$^2$ is C$_{1-6}$-alkyl, which is optionally substituted by one or more groups selected from among OH, COOR$^{2.1}$, CON(CH$_3$)$_2$, C$_{1-6}$-alkyl, phenyl, cyclopropyl and NR$^{2.2}$R$^{2.3}$, which may in turn optionally be substituted by one or more groups selected from among OH, fluorine, chlorine, bromine, iodine, OR$^{2.1}$, oxo, C$_{1-6}$-alkyl, phenyl, C$_{1-3}$-alkanol, CH—NR$^{2.2}$R$^{2.3}$ and NR$^{2.2}$R$^{2.3}$,
as well as pharmacologically acceptable salts, diastereomers, enantiomers, racemates, hydrates or solvates thereof.

The invention preferably also relates to the above method of preparing compounds according to formula 1, wherein:
R$^2$ is C$_{1-6}$-alkyl, which is substituted by one or more groups selected from among OH, phenyl, COOR$^{2.1}$, NH$_2$, while the phenyl may in turn optionally be substituted by one or more groups selected from among OH, fluorine, chlorine, bromine, iodine, OR$^{2.1}$, C$_{1-6}$-alkyl, CH$_2$—NH$_2$, CH$_2$(CH$_3$)$_2$, NH$_2$ and N(CH$_3$)$_2$, as well as pharmacologically acceptable salts, diastereomers, enantiomers, racemates, hydrates or solvates thereof.

The invention preferably also relates to the method of preparing compounds according to formula 1, wherein:
$R^2$ is a group according to formula 9

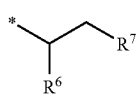

9 wherein
$R^7$ is OH or $NH_2$; and
$R^6$ is a group selected from among $C_{1-6}$-alkyl, $C_{5-10}$-heteroaryl and $C_{6-10}$-aryl, preferably phenyl, which may optionally be substituted by one or more groups selected from among halogen, OH, $COOR^{2.1}$, $OR^{2.1}$, $NH_2$, $C_{1-6}$-alkyl, $C_{1-6}$-haloalkyl and $C_{1-6}$-alkanol, as well as pharmacologically acceptable salts, diastereomers, enantiomers, racemates, hydrates or solvates thereof.

The invention preferably also relates to the method of preparing compounds of formula 1, wherein:
$R^2$ is a group according to formula 9

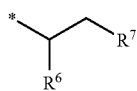

9 wherein
$R^7$ is OH or $NH_2$; and
$R^6$ is methyl, ethyl, propyl, isopropyl.

The invention preferably also relates to the method of preparing compounds of formula 1, wherein
$R^2$ is a monocyclic $C_{3-7}$-cycloalkyl ring which may be substituted in the spiro position by a group selected from among —OH, —$CH_2$—OH, —$CH_2$—$CH_2$—OH, branched or unbranched $C_{3-6}$-alkanol, —$OR^{2.1}$, methyl, ethyl, propyl, isopropyl, butyl, isobutyl and halogen, wherein $R^{2.1}$ may be selected from among methyl, ethyl, propyl, isopropyl, butyl, isobutyl.

The invention preferably also relates to the method of preparing compounds of formula 1, wherein:
$R^2$ denotes a group selected from among monocyclic, saturated three-, four-, five-, six- or seven-membered heterocycle with 1, 2 or 3 heteroatoms in each case selected from among N, O and S, which may optionally be substituted by one or more groups selected from among fluorine, chlorine, bromine, OH, oxo and SH or by one or more groups selected from among $OR^{2.1}$, $SR^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, $C_{5-10}$-heteroaryl-$C_{1-6}$-alkylene, $C_{5-10}$ heterocycle, $C_{5-10}$-heteroaryl and $NR^{2.2}R^{2.3}$, which may in turn optionally be substituted by one or more groups selected from among OH, $OR^{2.1}$, oxo, halogen, $C_{1-6}$-alkyl, phenyl and $NR^{2.2}R^{2.3}$,
wherein $R^{2.1}$ denotes H or a group selected from among $C_{1-6}$-alkyl, $C_{1-6}$-alkanol, $C_{1-3}$-haloalkyl, mono- or bicyclic $C_{3-10}$ cycloalkyl, phenyl-$C_{1-6}$-alkylene, mono- or bicyclic $C_{5-10}$-heteroaryl-$C_{1-6}$-alkylene, $C_{3-10}$ heterocycle-$C_{1-6}$-alkylene, $C_{3-7}$-cycloalkyl-$C_{1-6}$-alkylene, phenyl, a mono- or bicyclic $C_{5-10}$-heteroaryl and a monocyclic, saturated or unsaturated, five, six or seven-membered heterocycle with 1, 2 or 3 heteroatoms selected from among N, O and S, which may optionally be substituted by one or more groups selected from among OH, halogen, $C_{1-6}$-alkyl and phenyl, wherein $R^{2.2}$ and $R^{2.3}$ independently of one another are H or a group selected from among halogen, $C_{1-6}$-alkyl, mono- or bicyclic $C_{3-10}$ cycloalkyl, phenyl-$C_{1-6}$-alkylene, $C_{5-10}$-heteroaryl-$C_{1-6}$-alkylene, phenyl, mono or bicyclic $C_{3-10}$ heterocycle, mono- or bicyclic $C_{5-10}$-heteroaryl, CO—$NH_2$, CO—$NHCH_3$, CO—$N(CH_3)_2$, $SO_2$ ($C_1$-$C_2$-alkyl), CO—$R^{2.1}$ and $COOR^{2.1}$, which may optionally be substituted by one or more groups selected from among OH, halogen, $C_{1-6}$-alkyl, phenyl and $COOR^{2.1}$.

The invention preferably also relates to the method of preparing compounds according to formula 1, wherein:
$R^3$ denotes fluorine, chlorine, bromine, iodine or CN,
as well as pharmacologically acceptable salts, diastereomers, enantiomers, racemates, hydrates or solvates thereof.

The invention preferably also relates to the above method of preparing compounds according to formula 1, wherein:
$R^3$ denotes the group —CO—$NR^{3.1}R^{3.2}$,
wherein $R^{3.1}$ and $R^{3.2}$ independently of one another are H or groups selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{5-10}$ heterocycle, $C_{5-10}$ heterocycle-$C_{1-6}$-alkylene and mono- or bicyclic $C_{5-10}$-heteroaryl, while the group in each case may optionally be substituted by one or more groups selected from among OH, oxo, halogen, $C_{1-6}$-alkyl and O—$C_{1-6}$-alkyl,
as well as pharmacologically acceptable salts, diastereomers, enantiomers, racemates, hydrates or solvates thereof.

The invention preferably also relates to the method of preparing compounds according to formula 1, wherein:
$R^3$ denotes the group —CO—$NR^{3.1}R^{3.2}$,
wherein $R^{3.1}$ is hydrogen or methyl, and
$R^{3.2}$ denotes a group selected from among $C_{1-6}$-alkyl, $C_{2-6}$-alkenyl, $C_{2-6}$-alkynyl, $C_{6-10}$-aryl; $C_{6-10}$-aryl-$C_{1-6}$-alkylene, $C_{5-10}$-heteroaryl-$C_{1-6}$-alkylene, $C_{5-10}$-heteroaryl-$C_{1-6}$-alkynylene, $C_{5-10}$-heteroaryl-$C_{1-6}$-alkenylene, mono- or bicyclic, $C_{5-10}$ heterocycle, $C_{5-10}$ heterocycle-$C_{1-6}$-alkylene and mono- or bicyclic $C_{5-10}$-heteroaryl, while the group in each case may optionally be substituted by one or more groups selected from among OH, oxo, halogen, $C_{1-6}$-alkyl and O—$C_{1-6}$-alkyl,
as well as pharmacologically acceptable salts, diastereomers, enantiomers, racemates, hydrates or solvates thereof.

The invention preferably also relates to the method of preparing compounds according to formula 1, wherein:
$R^3$ denotes the group —CO—$NR^{3.1}R^{3.2}$,
wherein $R^{3.1}$ and $R^{3.2}$ independently of one another are H or groups selected from among $C_{1-6}$-alkyl, phenyl; phenyl-$C_{1-6}$-alkylene, $C_{5-6}$-heteroaryl-$C_{1-6}$-alkylene, $C_{5-6}$-heteroaryl-$C_{1-6}$-alkynylene, $C_{5-6}$-heteroaryl-$C_{1-6}$-alkenylene, mono- or bicyclic, $C_{5-10}$ heterocycle, $C_{5-10}$ heterocycle-$C_{1-6}$-alkylene and mono- or bicyclic $C_{5-10}$-heteroaryl, while the group may in each case optionally be substituted by one or more groups selected from among OH, oxo, halogen, $C_{1-6}$-alkyl and O—$C_{1-6}$-alkyl
as well as pharmacologically acceptable salts, diastereomers, enantiomers, racemates, hydrates or solvates thereof.

The invention preferably also relates to the method of preparing compounds according to formula 1, wherein:
$R^3$ denotes the group —$NR^{3.3}$—CO—$R^{3.4}$,
wherein $R^{3.3}$ is H or a group selected from among $C_{1-6}$-alkyl, $C_{2-6}$-alkenyl, $C_{6-10}$-aryl; $C_{6-10}$-aryl-$C_{1-6}$-alkylene, $C_{5-10}$-heteroaryl-$C_{1-6}$-alkylene, $C_{3-10}$ heterocycle and einem $C_{5-10}$-heteroaryl is, which may optionally be substituted by one or more groups ausgewählt aus der group bestehend aus OH, $OR^{2.1}$, oxo, $NH_2$, $NR^{2.2}R^{2.3}$, halogen, $C_{1-6}$-alkyl and $C_{6-10}$-aryl may be substituted, and wherein $R^{3.4}$ is H or a group selected from among $C_{1-6}$-alkyl, $C_{2-6}$-alkenyl, $C_{2-6}$-alkynyl, $C_{1-6}$-alkanol, $OR^{2.1}$, $CH_2$—O—CO—$C_{1-6}$-alkyl, $CH_2NR^{2.2}R^{2.3}$, $NR^{2.2}R^{2.3}$, $C_{6-10}$-aryl; $C_{6-10}$-aryl-$C_{1-6}$-alkylene, $C_{5-10}$-heteroaryl-$C_{1-6}$-alkylene, mono- or bicyclic, saturated or unsaturated $C_{3-10}$-heterocycle with 1, 2 or 3 heteroatoms selected from among O, S and N and a mono- or bicyclic $C_{5-10}$-heteroaryl with 1, 2 or 3 heteroatoms selected from among O, S and N, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, as well as pharmacologically acceptable salts, diastereomers, enantiomers, racemates, hydrates or solvates thereof.

The invention preferably also relates to the above method of preparing compounds according to formula 1, wherein:
$R^3$ denotes the group —$NR^{3.3}$—CO—$R^{3.4}$,
 wherein $R^{3.3}$ is hydrogen or methyl, and
 wherein $R^{3.4}$ denotes a group selected from among $C_{1-6}$-alkyl, $C_{2-6}$-alkenyl, $C_{2-6}$-alkynyl, $C_{1-6}$-alkanol, $OR^{2.1}$, $CH_2$—O—CO—$C_{1-6}$-alkyl, $CH_2NR^{2.2}R^{2.3}$, $NR^{2.2}R^{2.3}$, $C_{6-10}$-aryl; $C_{6-10}$-aryl-$C_{1-6}$-alkylene, $C_{5-10}$-heteroaryl-$C_{1-6}$-alkylene, mono- or bicyclic, saturated or unsaturated $C_{3-10}$-heterocycle with 1, 2 or 3 heteroatoms selected from among N; S and O and a mono- or bicyclic $C_{5-10}$-heteroaryl with 1, 2 or 3 heteroatoms selected from among N; S and O, which may optionally be substituted by one or more groups selected from among OH, $OR^{2.1}$, oxo, $NH_2$, $NR^{2.2}R^{2.3}$, halogen, $C_{1-6}$-alkyl and $C_{6-10}$-aryl, as well as pharmacologically acceptable salts, diastereomers, enantiomers, racemates, hydrates or solvates thereof.

The invention preferably also relates to the method of preparing compounds according to formula 1, wherein:
$R^3$ denotes the group —$NR^{3.3}$—CO—$R^{3.4}$,
 wherein $R^{3.3}$ is H or a group selected from among $C_{1-6}$-alkyl, phenyl; phenyl-$C_{1-6}$-alkylene, $C_{5-10}$-heteroaryl-$C_{1-6}$-alkylene, $C_{5-10}$-heterocycle and a $C_{5-10}$-heteroaryl, which may optionally be substituted by one or more groups selected from among OH, $OR^{2.1}$, oxo, $NH_2$, $N(CH_3)_2$, halogen, $C_{1-6}$-alkyl and phenyl, and
 wherein $R^{3.4}$ is H or a group selected from among $C_{1-6}$-alkyl, $C_{1-6}$-alkanol, $OR^{2.1}$, $CH_2$—O—CO—$C_{1-6}$-alkyl, $CH_2$—$NH_2$, $CH_2$—$N(CH_3)_2$, $NH_2$, $N(CH_3)_2$, phenyl; phenyl-$C_{1-6}$-alkylene, $C_{5-10}$-heteroaryl-$C_{1-6}$-alkylene, mono- or bicyclic, saturated or unsaturated $C_{5-10}$ heterocycle with 1, 2 or 3 heteroatoms selected from among N; S and O and a mono- or bicyclic $C_{5-10}$-heteroaryl with 1, 2 or 3 heteroatoms selected from among N; S and O, which may optionally be substituted by one or more groups selected from among OH, $OR^{2.1}$, oxo, $NH_2$, $N(CH_3)_2$, halogen, $C_{1-6}$-alkyl and phenyl, as well as pharmacologically acceptable salts, diastereomers, enantiomers, racemates, hydrates or solvates thereof.

The invention preferably also relates to the above method of preparing compounds according to formula 1, wherein $R^4$ and $R^5$ are H or methyl.

Preferably, this invention relates to a method to prepare the compound of formula 1, wherein
$R_A$ denotes

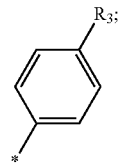

Z denotes a halogen;
X denotes SO;
$R^1$ denotes H or methyl;
$R^2$ is H or a group selected from among $C_{1-10}$-alkyl, $C_{2-6}$-alkenyl and $C_{2-6}$-alkynyl, which may optionally be substituted by halogen and which may optionally be substituted by one or more groups selected from among $OR^{2.1}$, $COOR^{2.1}$, $CONR^{2.2}R^{2.3}$, $SR^{2.1}$, $C_{6-10}$-aryl, a mono- or bicyclic $C_{3-10}$ heterocycle, a mono- or bicyclic $C_{5-10}$-heteroaryl, a mono- or bicyclic $C_{3-10}$-cycloalkyl, $CH_2$—$NR^{2.2}R^{2.3}$ and $NR^{2.2}R^{2.3}$, which may in turn optionally be substituted by one or more groups selected from among OH, halogen, $OR^{2.1}$, oxo, $C_{1-6}$-alkyl, $C_{6-10}$-aryl, $COOR^{2.1}$, $CH_2$—$NR^{2.2}R^{2.3}$ and $NR^{2.2}R^{2.3}$,
 while $R^{2.1}$ is H or a group selected from among $C_{1-6}$-alkyl, $C_{1-6}$-alkanol, $C_{1-3}$-haloalkyl, mono- or bicyclic $C_{3-10}$ cycloalkyl, $C_{6-10}$-aryl-$C_{1-6}$-alkylene, mono- or bicyclic $C_{5-10}$-heteroaryl-$C_{1-6}$-alkylene, $C_{3-10}$-heterocycle-$C_{1-6}$-alkylene, $C_{3-10}$-cycloalkyl-$C_{1-6}$-alkylene, a mono- or bicyclic $C_{6-10}$-aryl, a mono- or bicyclic $C_{5-10}$-heteroaryl and a mono- or bicyclic, saturated or unsaturated heterocycle, which may optionally be substituted by one or more groups selected from among OH, halogen, $C_{1-6}$-alkyl and $C_{6-10}$-aryl, while $R^{2.2}$ and $R^{2.3}$ independently of one another are H or a group selected from among halogen, $C_{1-6}$-alkyl, mono- or bicyclic $C_{3-10}$ cycloalkyl, $C_{6-10}$-aryl-$C_{1-6}$-alkylene, $C_{5-10}$-heteroaryl-$C_{1-6}$-alkylene, mono- or bicyclic $C_{6-10}$-aryl, mono- or bicyclic $C_{3-10}$ heterocycle, mono- or bicyclic $C_{5-10}$-heteroaryl, CO—$NH_2$, CO—$NHCH_3$, CO—$N(CH_3)_2$, $SO_2(C_1$-$C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$,
or $R^2$ denotes a mono- or polycyclic $C_{5-10}$-cycloalkyl, which may optionally be bridged by one or more $C_{1-3}$-alkyl groups and which may optionally be mono- or polysubstituted by OH or halogen or by one or more groups selected from among branched or unbranched $C_{1-3}$-alkanol, $OR^{2.1}$, $COOR^{2.1}$, $SO_2NR^{2.2}R^{2.3}$, $C_{5-10}$ heterocycle, phenyl, $C_{1-6}$-alkyl, phenyl-$C_{1-6}$-alkylene, $C_{5-6}$-heteroaryl-$C_{1-6}$-alkylene, mono- or bicyclic $C_{5-10}$-cycloalkyl and $NR^{2.2}R^{2.3}$, which may optionally be substituted by one or more groups selected from among OH, $OR^{2.1}$, oxo, halogen, $C_{1-6}$-alkyl, phenyl and $NR^{2.2}R^{2.3}$,
or wherein $NR^1R^2$ together denote a heterocyclic $C_{4-7}$ ring, which may optionally be bridged, which contains 1, 2 or 3 heteroatoms selected from among N, O and S and which may optionally be substituted by one or more groups selected from among OH, $OR^{2.1}$, $C_{1-6}$-alkanol, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}$-2.3, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$ and $NR^{2.2}R^{2.3}$;
$R^3$ denotes fluorine, chlorine, bromine, iodine or CN; and
$R^4$ and $R^5$ are independently selected from H and $C_{1-6}$-alkyl.

In another preferred embodiment, this invention relates to a method to prepare the compound of formula 1, wherein $R_A$ denotes

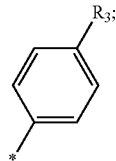

$R^2$ is $C_{1-10}$-alkyl, which may optionally be substituted by one or more groups selected from among $OR^{2.1}$, $COOR^{2.1}$ and $C_{6-10}$-aryl, wherein $R^{2.1}$ is H,
or $R^2$ denotes a monocyclic $C_{5-10}$-cycloalkyl,
or wherein $NR^1R^2$ together denote a heterocyclic $C_{4-7}$ ring.

In yet another preferred embodiment, this invention relates to a method to prepare the compound of formula 1, wherein $R_A$ denotes

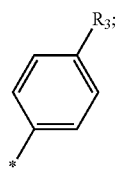

Z denotes chloride;
X denotes SO;
$R^1$ denotes H; and
$R^4$ and $R^5$ are independently H or methyl.

In yet another preferred embodiment, this invention relates to a method to prepare the compound of formula 1, wherein $R_A$ denotes

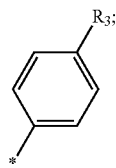

Z denotes chloride;
X denotes SO;
$R^1$ denotes H;
$R^3$ denotes chloride; and
$R^4$ and $R^5$ are independently H or methyl.

The invention preferably also relates to the above method of preparing compounds according to formula 1, wherein:
$R^1$ is H;
$R^2$ is selected from among H, methyl, ethyl, propyl,

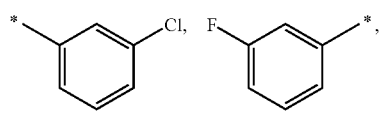

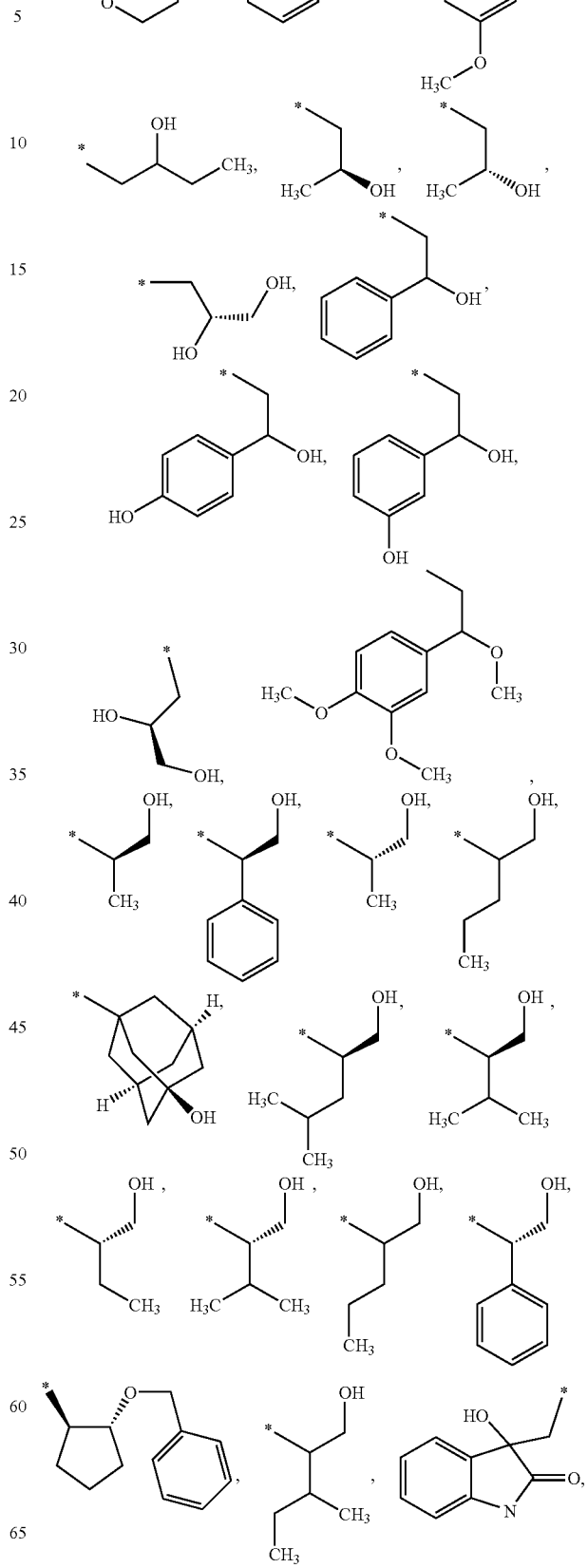

-continued
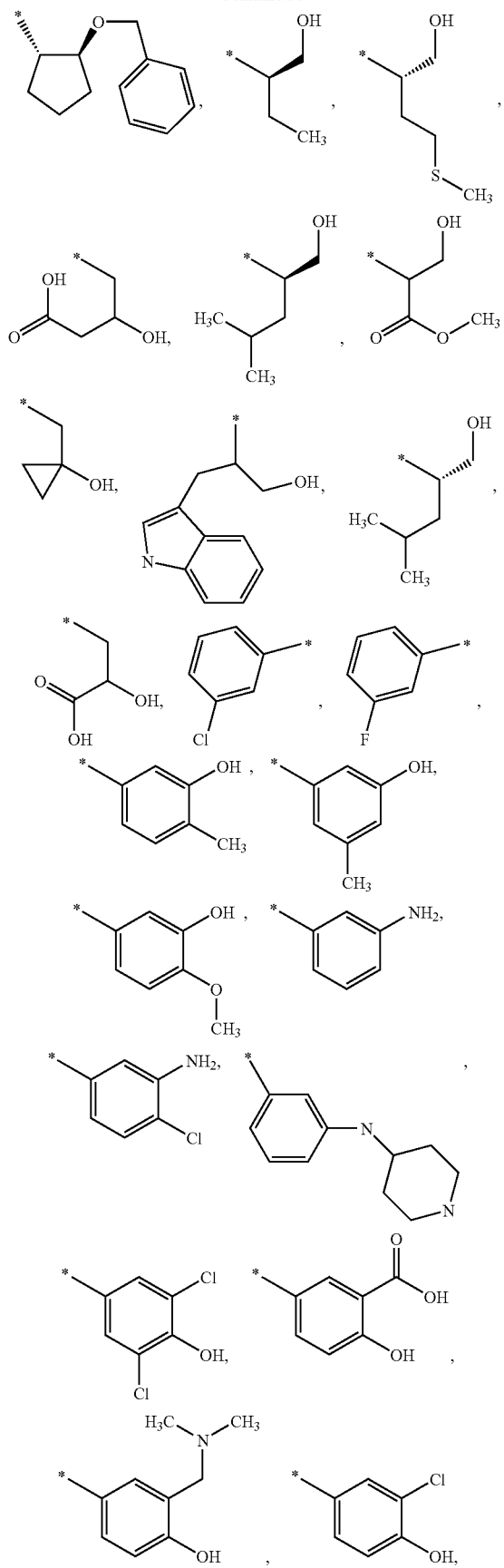
-continued
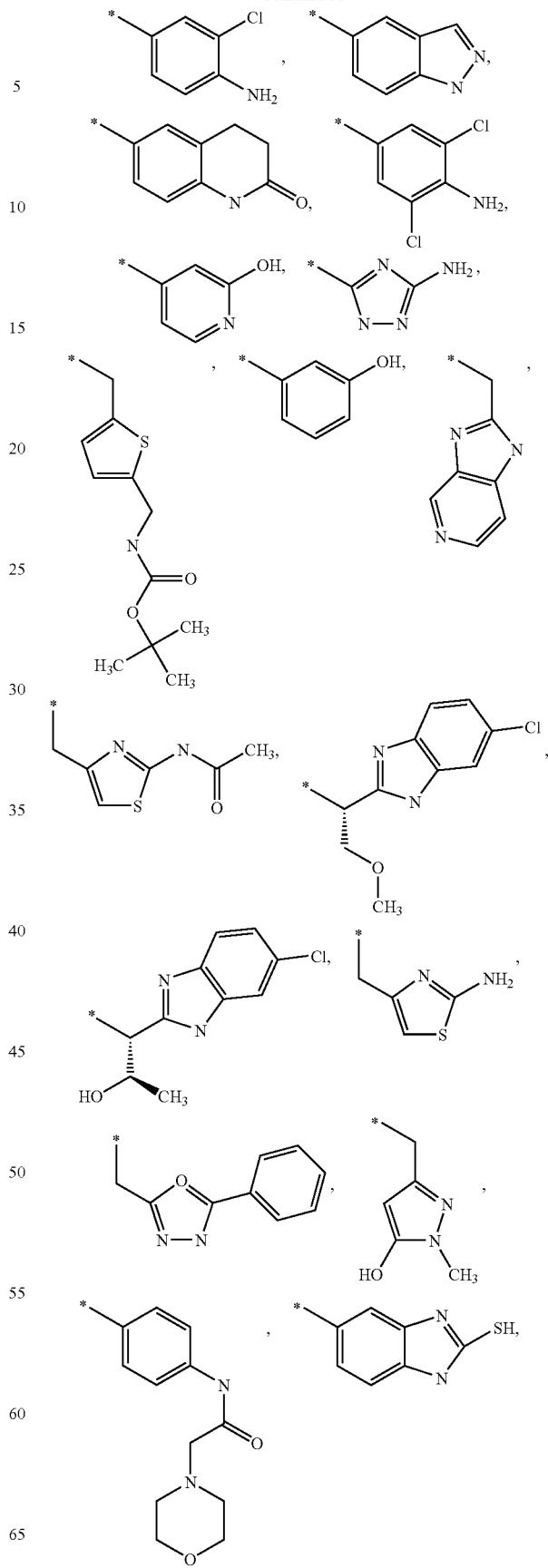

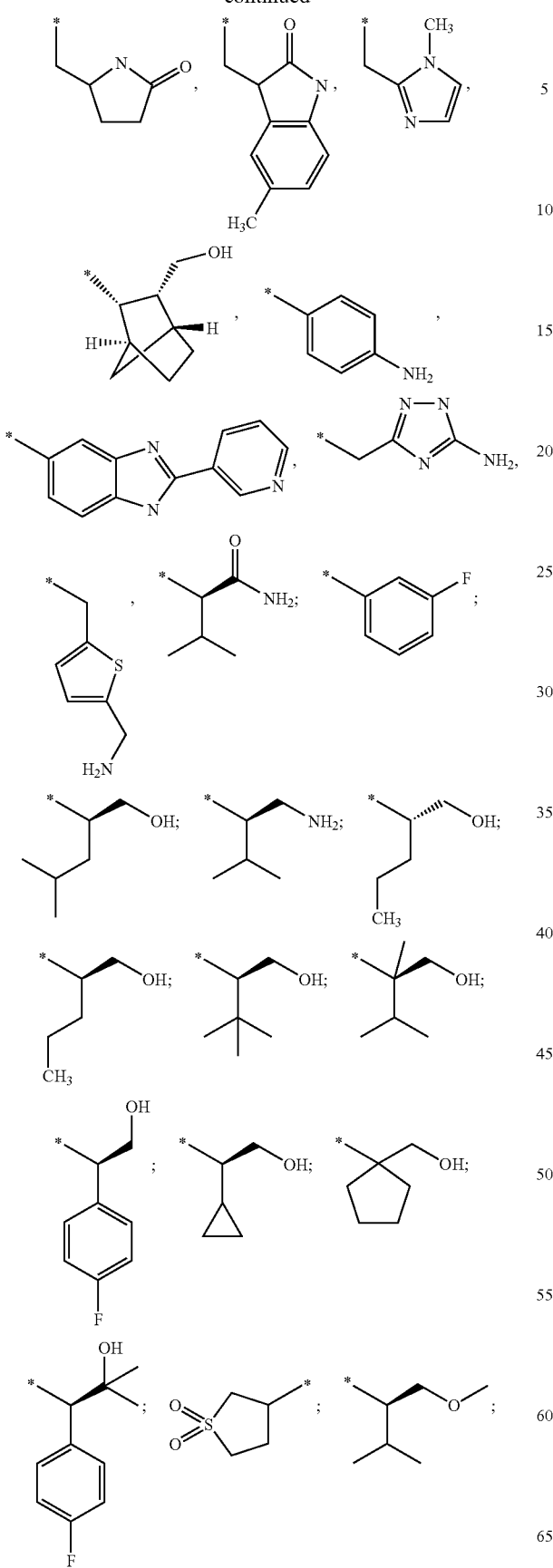
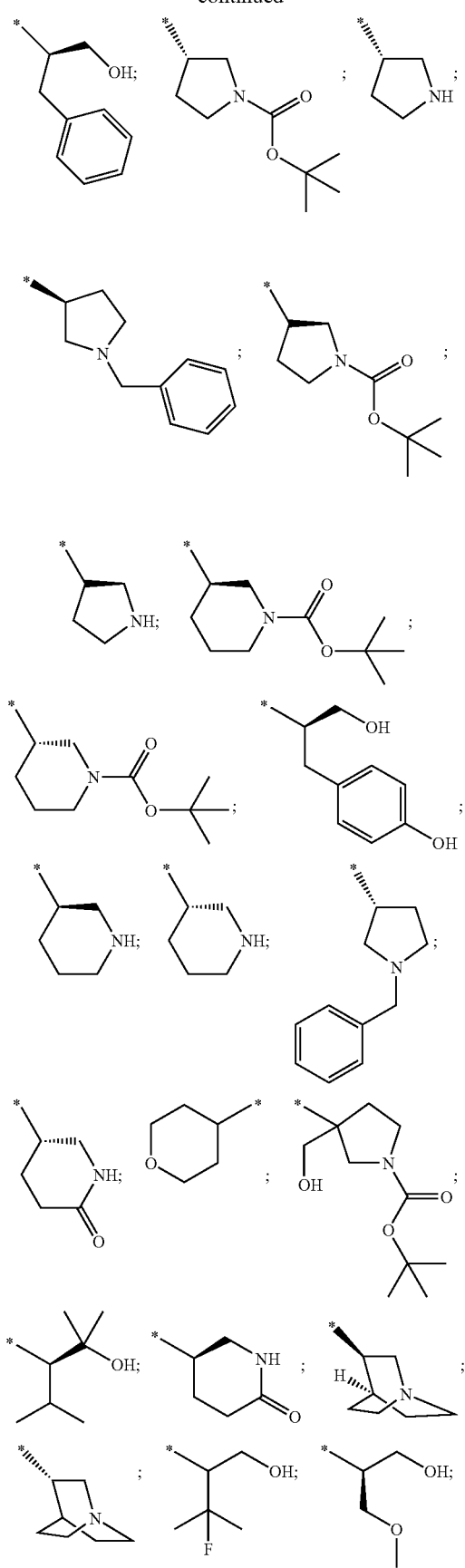

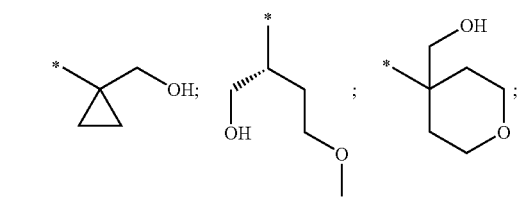
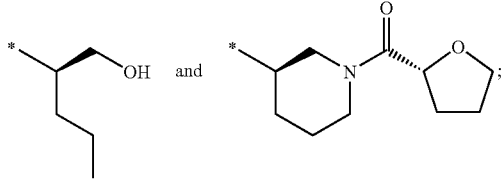
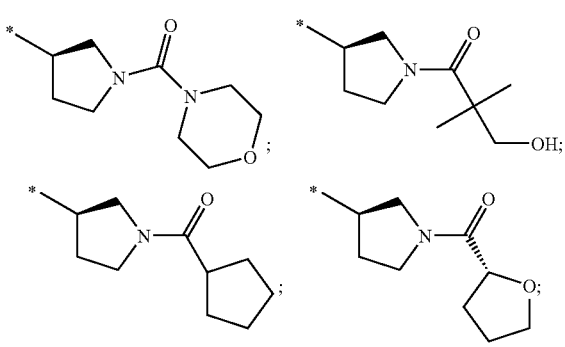
$R_A$ denotes
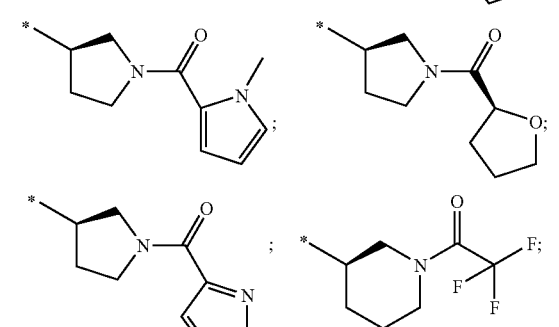
and
$R^3$ is selected from among chloride, cyanide,
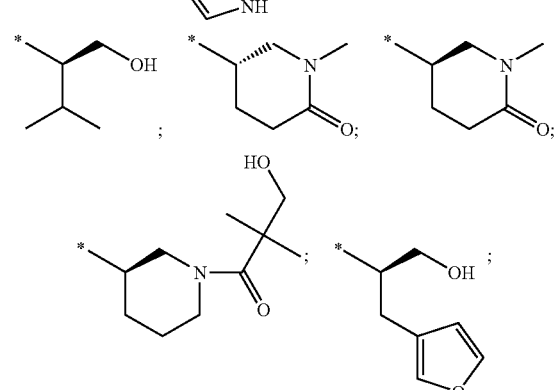
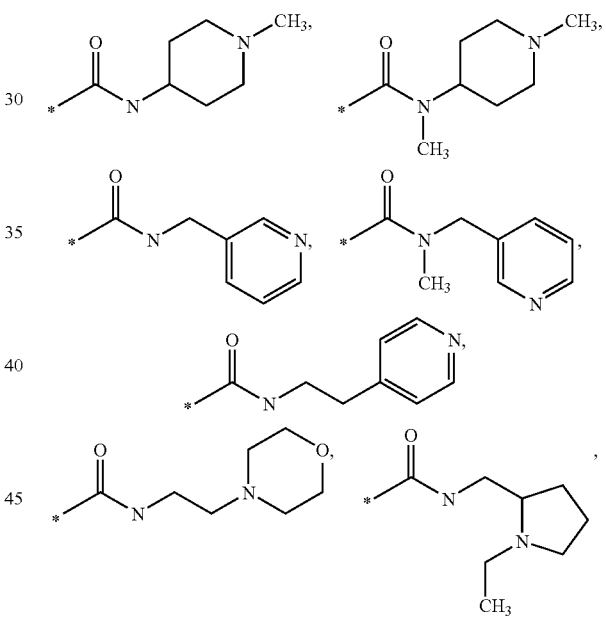
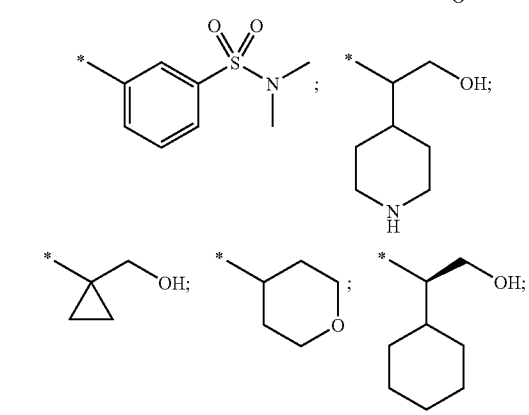
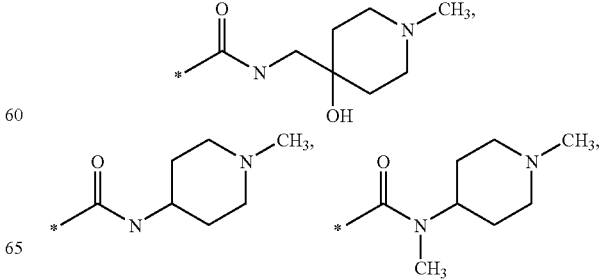

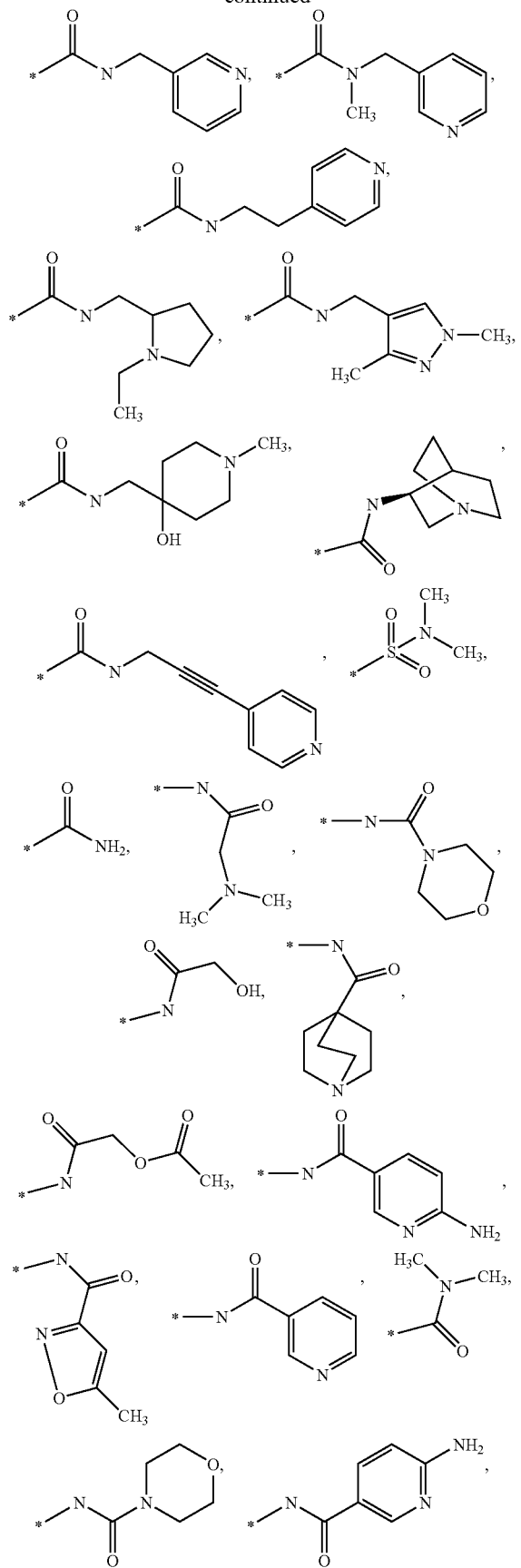
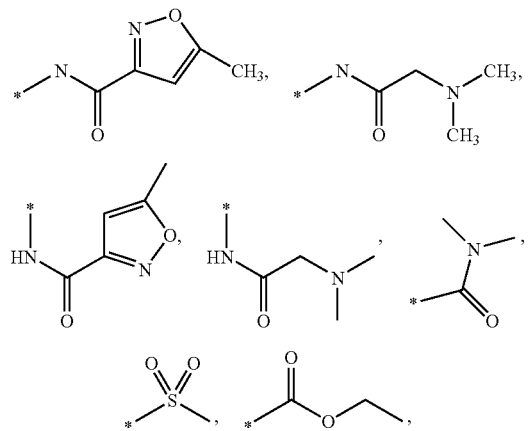
and bromide,
as well as pharmacologically acceptable salts, diastereomers, enantiomers, racemates, hydrates or solvates thereof.
The invention preferably also relates to the above method of preparing compounds according to formula 1, wherein:
$R^1$ is H;
$NR^1R^2$ is selected from among
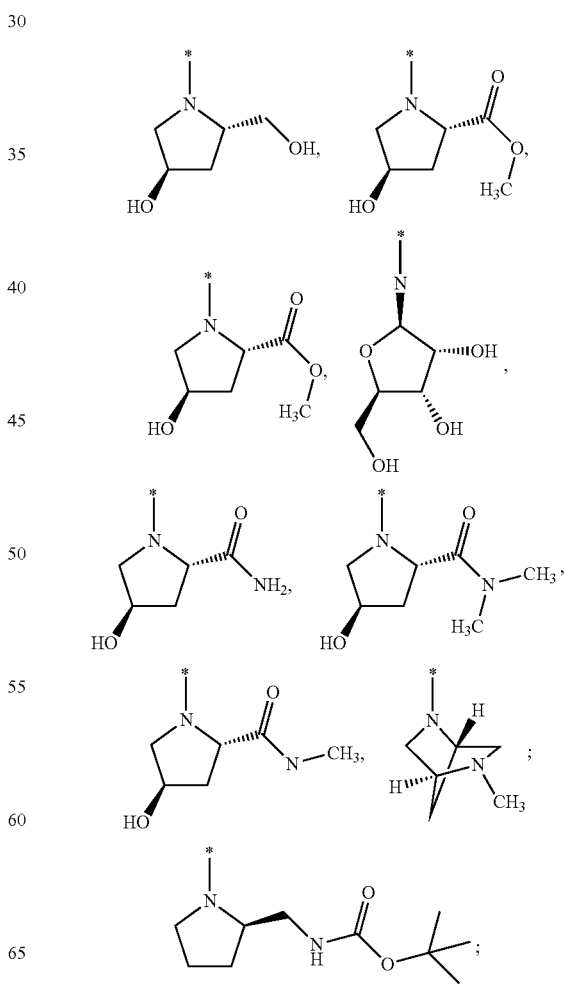

-continued
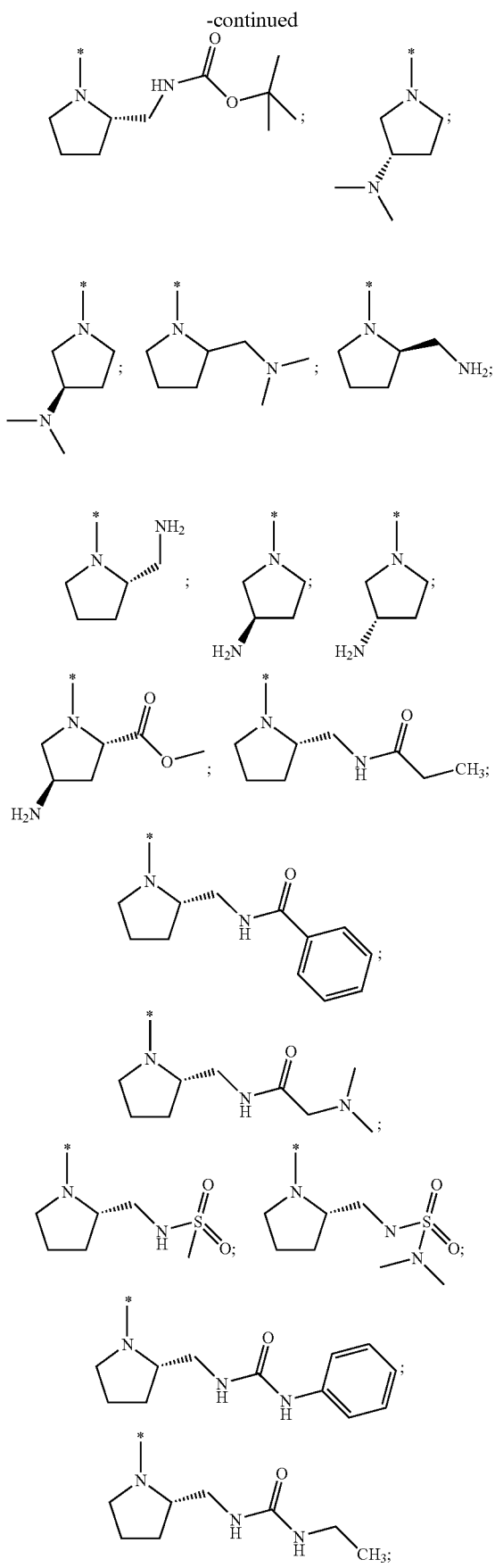
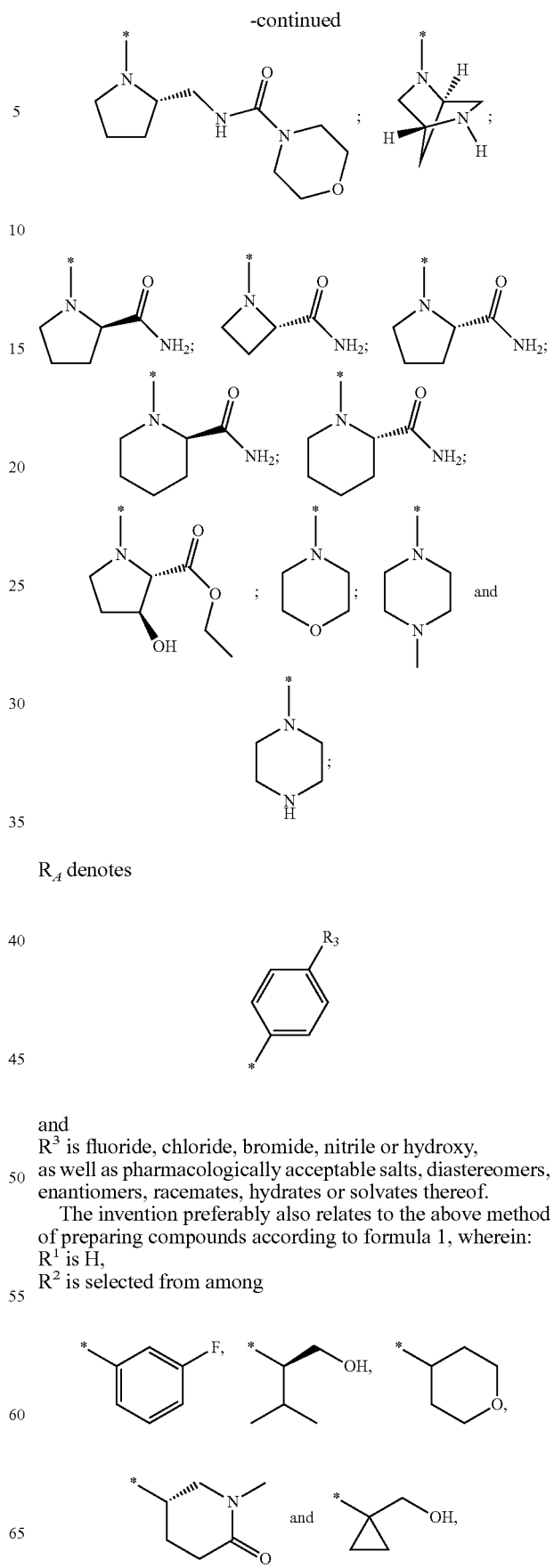
$R_A$ denotes
and
$R^3$ is fluoride, chloride, bromide, nitrile or hydroxy,
as well as pharmacologically acceptable salts, diastereomers, enantiomers, racemates, hydrates or solvates thereof.
The invention preferably also relates to the above method of preparing compounds according to formula 1, wherein:
$R^1$ is H,
$R^2$ is selected from among $R_4$ is selected from among

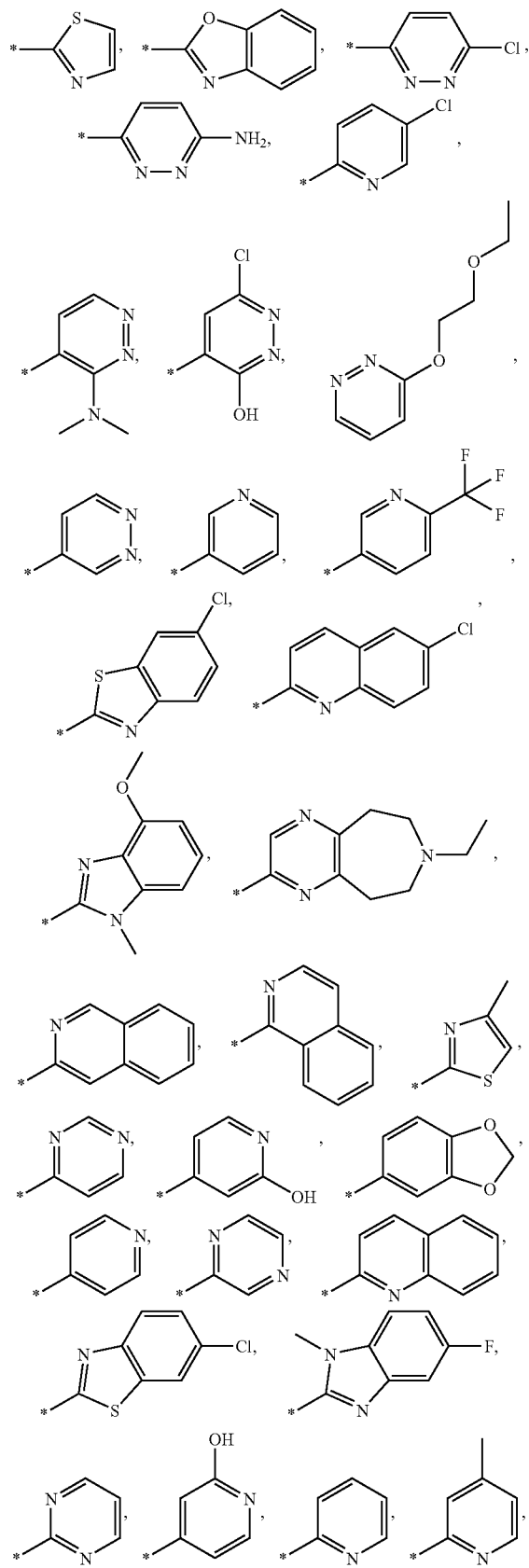

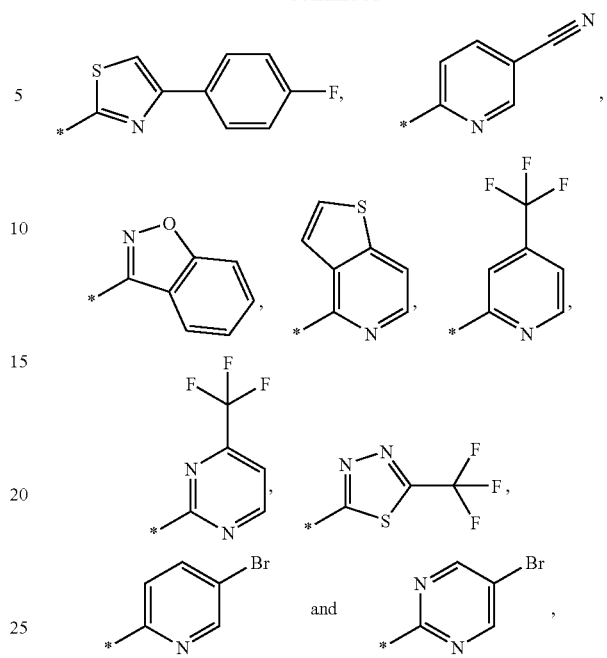

as well as pharmacologically acceptable salts, diastereomers, enantiomers, racemates, hydrates or solvates thereof.

Methods to Prepare Compounds of Formula I and Intermediates Used Therein

The present invention is directed to a method of preparing compounds of formula 1, dihydrothienopyrimidines, and intermediate compounds used in the synthesis of the same. The method of the present invention is particularly useful for the large-scale synthesis of dihydrothienopyrimidines because an intermediate compound of formula 6 (see Scheme 1) can be formed from a starting thioester and an α,β-unsaturated ester without the need for chromatographic purification in subsequent reaction steps. Another advantage of the method of the present invention is that the intermediate compound of formula 4 already has the substituted 4-phenylpiperazin-1-yl moiety at the 2-position, thus the 4-hydroxyl group can be converted to a halo group and then aminated to obtain the desired 4-substituted 2-(4-phenylpiperazin-1-yl) dihydrothienopyrimidine. As such, the present method overcomes limitations in the prior art, which discloses the creation of a 2,4-dihalo-dihydrothienopyrimidine intermediate, that is then aminated with two different substituents. The prior art method causes the formation of undesirable regioisomers that necessitates purification by chromatography, which in turn (a) prohibits large-scale synthesis and (b) greatly reduces the overall yield of the desire product. In contrast, the intermediate of formula 4 in the present method can be converted to the corresponding 4-halide and alkylated with a desirable amine to obtain the desired product (formula 1) without the need for chromatographic purification. Finally, stereoselective oxidation of formula 3 to formula 2 or formula 8 to formula 1 may be achieved. None of the steps in the present synthetic method requires extremely high or low temperatures, which can be difficult, costly and potentially dangerous to perform in a large-scale synthesis. Similarly, none of the presently disclosed reactions requires microwave radiation, which is not feasible in large-scale synthesis.

General Synthesis
SCHEME 1:
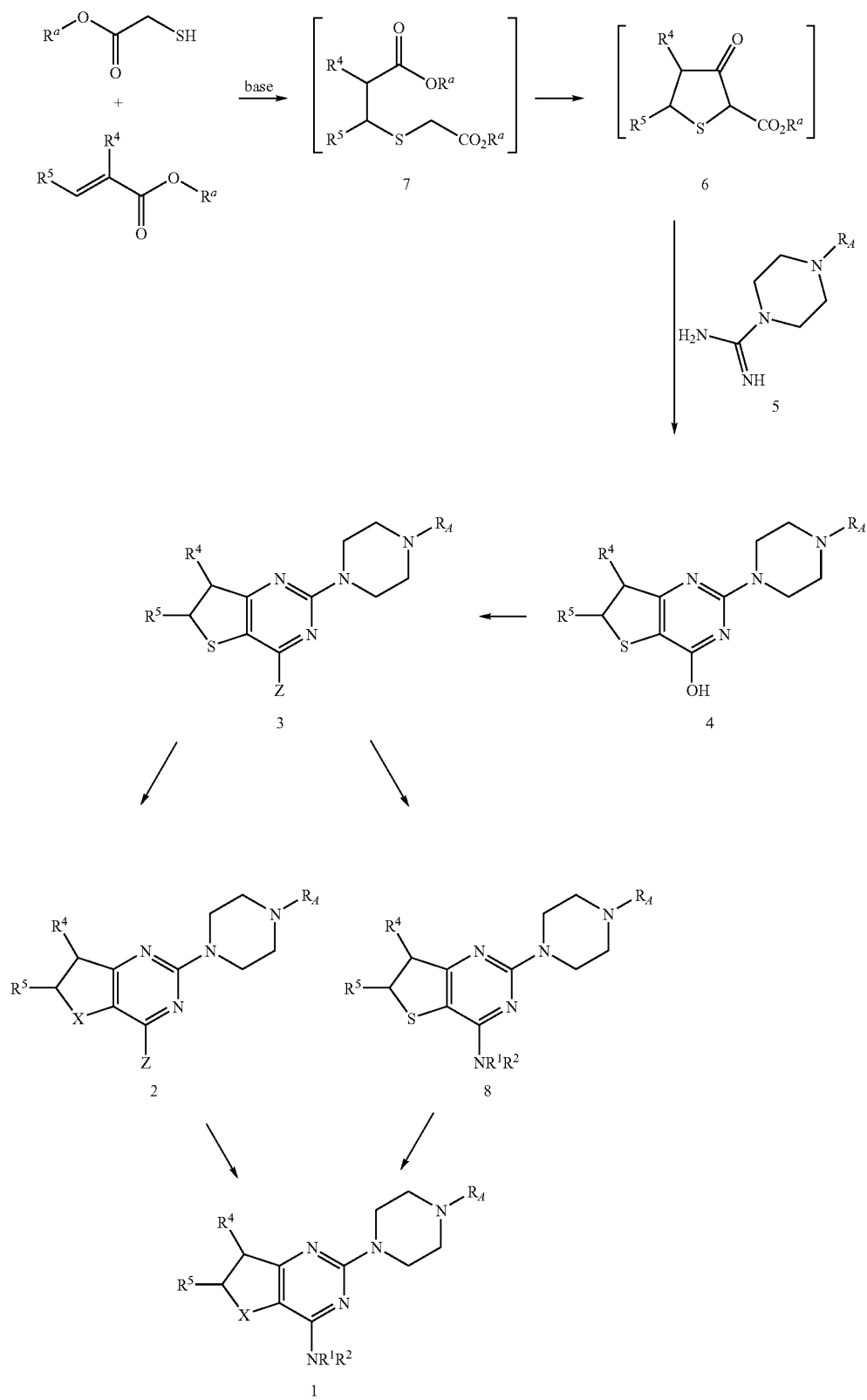

Scheme 1 illustrates the general method of synthesis of compounds of formula 1, wherein $R_A$, $R^a$, $R^1$-$R^5$, Z and X are as defined herein.

Dialkyl 3-thiaadipate is formed by reacting the corresponding alkyl 2-thioethylester with an α,β-unsaturated alkyl ester in the presence of a base. The base is preferably an organic base and preferably only a catalytic amount is used. One skilled in the art would be familiar with many organic bases suitable for this reaction. Preferable bases include tertiary and secondary amines, such as triethyl amine and piperidine, with piperidine being the most preferred.

Without the need for distillation or chromatographic purification, the dialkyl 3-thiaadipate can be cyclized to an alkyl 3-oxotetrahydrothiophene-2-carboxylate in the presence of an amine base and an organometallic catalyst or Lewis acid, such as $TiCl_4$, $(i-PrO)_2TiCl_2$, $(i-PrO)_3TiCl$ and $(i-PrO)TiCl_3$. For example, $Ti(OR)_nCl_m$, where R is alkyl and n=1-3 and m+n=4, may be used. A preferred Lewis acid is $TiCl_3(OiPr)$. It is also possible to use chiral variants of the aforementioned catalysts, by adding chrial ligands such as BINOL, substituted BINOLs, chrial diols, BINAP, DuPhos, Taddols, and tartrates. Other possible reagents which are known to promote regioselective Dieckman condensations are compounds or Lewis acids of the following formulas: $SnX_4$, $CuX_2$ and $NiX_2$, wherein X is selected from Cl, Br and —OTf. This is not an exhaustive list, and a skilled artisan would be aware of other suitable organometallic catalysts. Suitable amine bases would be known to a skilled artisan. However, tertiary amine bases are preferable, for example, triethylamine and diisopropyl-ethylamine. A preferable solvent is dichloromethane. Other solvents can also be used, such as toluene, chloroform and $CCl_4$. If an acid quench is used, acids such as, but not limited to, HCl or $H_2SO_4$ may be used. Filtration through $MgSO_4$ can be omitted or replaced by a filtration through different media such as $Na_2SO_4$, celite, charcoal and so on. The temperature range of carrying out this reaction is between 0° C. to −78° C. This method of preparing the intermediates of formula 6 ensures that the subsequent step or the entire synthesis may be performed without requiring any chromatographic purification.

Without any high vacuum distillation or chromatographic purification, the alkyl 3-oxotetrahydrothiophene-2-carboxylate can be reacted with a guanidine intermediate to form the intermediate compound of formula 4. This reaction is performed in the presence of a base. Skilled artisans would know of suitable bases for this reaction. Preferably the base is an organometallic base, such as t-BuOK, t-BuONa, $NaOCH_3$, NaOEt, n-BuLi, t-BuLi, NaOH or NaH can be used in combination with other solvents (e.g., MeOH, i-PrOH, t-BuOH). The most preferred base is $NaOCH_3$. Other organic amine bases such as pyridine, pyrrolidine, triethylamine, or DIPEA may also be used. Many different organic solvents can be used in this reaction. A skilled artisan would know which would be suitable for this reaction, particularly in view of the chosen base. If $NaOCH_3$ is used as the base, it is preferable to use methanol as the solvent. This reaction is typically heated above room temperature, and more preferably the reaction is heat to about 60° C. or more, or in the case of methanol being the solvent, the reaction is preferably heated to reflux. If an acid quench is used, this may be carried out in acids such as HCl, $H_2SO_4$ or AcOH. The cyclocondensation occurs with various salt forms of the guanidine and its free base.

Without chromatographic purification, intermediate 4 can then be converted to intermediate 3. For example, the hydroxyl group can converted to a sulfonyl or sulfonated leaving group, such as a tosylate, a mesylate, a besylate, a brosylate, a triflate or a nosylate. Alcohols may be converted to the corresponding halide using many different reagents and reaction conditions, and a skilled artisan would be familiar with such, since the literature is replete with examples. One possibility is using a reagent of the formula $POZ_3$, wherein Z is a halogen. Converting the hydroxyl group to a halide is the preferred method. The most preferred halide is wherein Z is Cl. Preferred reagents for this reaction are $POCl_3$, $SOCl_2$, $SO_2Cl_2$, $(COCl)_2$, $PCl_5$, $POCl_3/PCl_5$, $Cl_2$ and NCS. Another possibility relates to attaching a leaving group to position of the hydroxyl group. Suitable leaving groups include F and non-halide leaving groups, include, but are not limited to, $NO_2$ and N2. Solvents may vary depending on the reagent chosen, but when using $POCl_3$, an aprotic organic solvent is best, such as $CH_3CN$, $CH_2Cl_2$, toluene, $CHCl_3$ and diethylether. For large-scale synthesis, preferably $CH_3CN$ is used as the solvent. This reaction may be performed at room temperature, but it is preferable to heat the reaction to about 50° C. or greater, and more preferable to heat it to about 60° C. or more. Similarly, a skilled artisan would know of reagents and conditions to convert a hydroxyl group to a sulfonyl leaving.

Typically, this done using the corresponding sulfonyl halide, for example tosylchloride can be used to form a tosylate.

Without chromatographic purification, intermediate 3 can be aminated with a desired substituted amine ($NR^1R^2$) under basic conditions to obtain a dihydrothienopyrimidine compound of formula 8. Suitable bases for this reaction include, but are not limited to, amines, NaH, t-BuONa, t-buOK, DBU, $KN(TMS)_2$, $NaN(TMS)_2$, $LiN(TMS)_2$, and LDA. Other bases include $i-Pr_2NEt$, $Et_3N$, morpholine and pyridine. Preferred bases for this reaction are tertiary amino bases, such as triethylamine and diisopropylethylamine A skilled artisan would know suitable solvents for this reaction, e.g, THF, diglyme, DMSO, NMP, DMAc, acetonitrile and water. A preferable solvent is DMSO. This reaction can be performed at room temperature, but it is preferable to heat it to about 60° C. or more and more preferably to about 80° C.

The dihydrothienopyrimidine compound of formula 8 can be oxidized. Oxidation of sulfides can be accomplished using many different reagents and conditions and a skilled artisan would know such, since the literature is replete with examples. Also, a skilled artisan would know of chiral catalysts that could be used in the oxidation reaction to achieve enantioselectivity. For example, the stereoselective oxidation may be carried out in the presence of a chiral ligand/metal or stoichiometric oxidant and a solvent. The chiral ligand/metal may be Ti/BINOL, substituted BINOL, $WO_3$/chiral ligand, Davis oxaziridine, D-epoxone/oxone, Mn/Salen, Ti/hydrobenzoin variants, Ti/mandelic acid, TiDET, $V(acac)_2$ or $Fe(acac)_3$/chiral ligand, whereas the stoichiometric oxidant may be cumene hydroperoxide, hydrogen peroxide, t-butyl hydroperoxide solution, MCPBA, peroxybenzoic acids, oxone or dioxiranes. Hydroperoxide solutions can be made in solvents, e.g., decane, nonane, toluene and water. Suitable solvents for this reaction include toluene, methylene chloride, chloroform, acetonitrile, THF or fluorobenzene, for example. Preferably the oxidation is performed using t-butylhydroperoxide, and more preferably the oxidation is performed using t-butylhydroperoxide, $Ti(i-PrO)_4$ and (S)-hydrobenzoin to obtain the R-enantiomer in high excess.

Alternatively, without chromatographic purification, intermediate 3 can be oxidized, as described above, to obtain an intermediate compound of formula 2. Thereafter, the intermediate compound of formula 2 can be aminated with a substituted amine, as described above, to obtain the desired compound of formula 1.

Specific Syntheses

SCHEME 2:

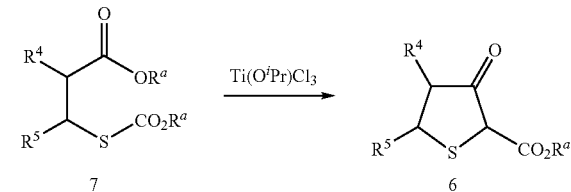

$R^4 = H$, $R^5$ and $R^a = H$, alkyl, aryl or heterocycle groups

Scheme 2 illustrates the practical and regioselective synthesis of 3-oxo-tetrahydrothiophene-2-carboxylic acid esters. The use of a Lewis acid catalyst, e.g., Ti(O$^i$Pr)Cl$_3$, instead of a base like NaOMe, NaH, R$_3$N, etc., ensures that the formation of 6 is selective and formation of an undesired regioisomer (see, e.g., a3 of Eqn. 1) is eliminated. This regioselective formation eliminates the need for a labor intensive chromatographic separation, and increases the overall yield of the desired isomer 6. Additionally, elimination of basic conditions during the reaction and workup prevent downstream product decomposition. The use of Ti(O$^i$Pr)Cl$_3$ is particularly useful for avoiding formation of chlorinated and elimination products that arise when other Lewis acids like TiCl$_4$ are used.

SCHEME 3:

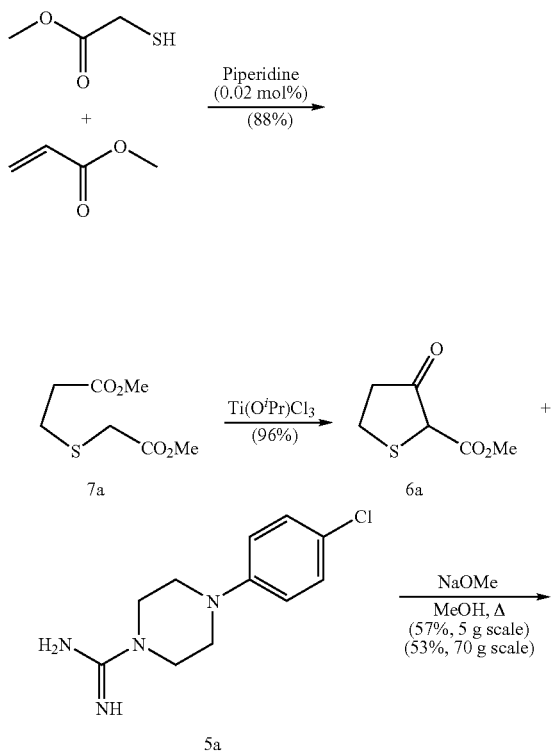

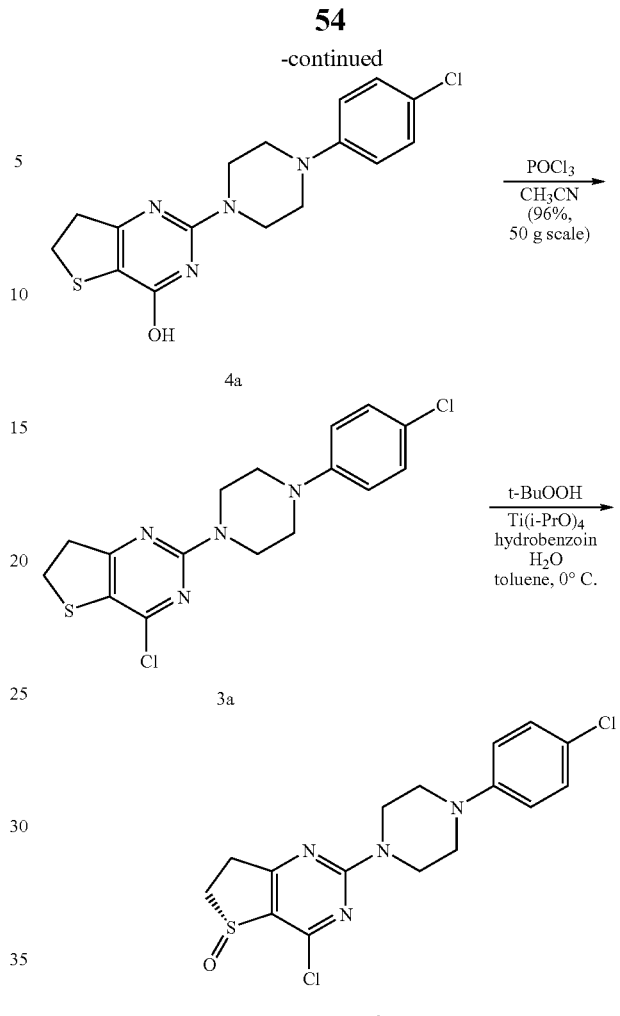

The following experimentals pertain to the specific synthesis illustrated in Scheme 3.

4-(4-chloro-phyenyl)-piperazine-1-carboxamide (5a)

To a suspension of 20.01 g 1-(4-chlorophenyl)piperazine in 60 mL of ethanol, add 10.44 g of pyrazole-1-carboxamidine hydrochloride and 55 mL of diisopropylethylamine. The reaction is then stirred to reflux. After 6 h, additional 1.50 g of pyrazole (0.14 g) is charged. After refluxing for an additional 1 h, the reaction mixture is allowed to cool to ambient temperature. The cloudy mixture is concentrated to approximately half of the volume. Water (30 mL) is charged and the mixture is stirred overnight. The white solid is filtered, rinsed with water (2×10 mL) and dried under reduced pressure at 50° C., which yields 11.88 g of 4-(4-chloro-phyenyl)-piperazine-1-carboxamide as a white solid. The cloudy filtrate is further concentrated and a second recovery of product is precipitated and dried to afford 5.13 g of 4-(4-chloro-phyenyl)-piperazine-1-carboxamide (99% overall yield).

Methyl 3-oxotetrahydrothiophene-2-carboxylate (6a)

Charge TiCl$_4$ (668 mL of a 1.0 M CH$_2$Cl$_2$) into an inert and dry 2 L jacketed reactor equipped with temperature probe, mechanical stirrer and a dropping funnel. Cool the solution to −10° C. Charge isopropanol (51 mL) at −10° C. and stir the mixture for 30 min Charge a solution of dimethyl 3-thiaadipate (methyl 3-[(2-methoxy-2-oxoethyl)thio]propanoate, (7a, 120 g) and $CH_2Cl_2$ (500 mL) slowly over 1 h keeping the internal temperature at or below −10° C. Stir the reaction mixture for 30 min at −10° C. Charge $Et_3N$ (287 mL) dropwise over 1 h keeping the internal temperature at or below −10° C. Upon complete addition, stir for 1-2 h then cool the mixture to −10° C. and charge 3 N HCl (approx. 800 mL). Warm the mixture to 30° C. and stir vigorously for a minimum of 1 h. Collect the organic layer and extract the aqueous with dichloromethane twice (approx. 500 mL per wash). Wash the combined organic portion with water twice (approx. 500 mL). Filter the solution through a thin pad of $MgSO_4$, rinse with dichloromethane. Remove the volatiles by distillation (temp=25° C., press=35 ton) to yield a brown oil (116 g, 75% assay, 87% yld.). Use the crude material immediately or store it under a blanket of nitrogen or argon and keep refrigerated until ready for use. The product is approximately a 12:1 mixture of keto:enol tautomers by NMR. $^1$H NMR (400 MHz, $CDCl_3$) keto tautomer: δ 4.03 (s, 1H), 3.77 (s, 3H), 3.31 (ddd, J=7.5, 8.0, 11.5 Hz, 1H), 3.05 (ddd, J=3.5, 8.0, 11.5 Hz, 1H), 2.84 (ddd, J=3.5, 7.5, 18.0 Hz, 1H), 2.66 (ddd, J=8.5, 8.5, 18.0 Hz, 1H; enol tautomer: 10.47 (s, 1H), 3.80 (s, 3H), 3.13 (dd, J=8.5, 8.5 Hz, 2H), 2.95 (dd, J=8.5, 8.5 Hz, 2H); GCMS for $C_6H_8O_3S$ (M$^+$): calcd. 160, obsvd. 160.

In addition, the following analogs are prepared by the experimental method just described:

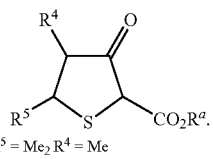

$R^5$ = Me $R^5$ = Et $R^5$ = Ph $R^5$ = Me$_2$ $R^4$ = Me

2-[4-(4-Chloro-phenyl)-piperazin-1-yl]-6,7-dihydro-thieno[3,2-d]pyrimidin-4-ol (4a)

Charge guanidine (5, 70 g) into an inerted reactor equipped with a cooling jacket, thermocouple thermometer, mechanical stirrer and $N_2$ line. Charge methanol (140 mL). Charge a 25% NaOMe solution in methanol (224 mL). Charge methyl 3-oxotetrahydrothiophene-2-carboxylate (6a, 62.1 g) into the reactor. Stir for 3-7 h at reflux. Cool the mixture to 22-25° C. Slowly neutralize the rxn. mixture to pH=6 with the above 2 M HCl (approx. 250 mL solution. Stir the mixture at 22-25° C. for 3 h (minimum). Collect the resulting solid by filtration. Wash the cake with isopropanol 2 times (approx. 50 mL per wash) and 2-5 times (approx. 50 mL per wash) with water. Air-dry the cake in the filter funnel for a minimum of 2 h. Dry in a vacuum oven under reduced pressure overnight at 50° C. to afford 56.2 g (55%) of product as an off white solid. $^1$H NMR (400 MHz, $CDCl_3$) δ 11.51 (s, 1H), 7.25-7.35 (m, 2H), 6.95-7.05 (m, 2H), 3.70-3.76 (m, 2H), 3.16-3.24 (m, 4H), 3.25 (dd, J=8.0, 8.0 Hz, 2H), 3.07 (dd, J=8.5, 8.5 Hz, 2H); $^{13}$C NMR (400 MHz, $CDCl_3$) δ 150.5, 129.6, 123.7, 118.1, 48.6, 45.3, 38.5, 28.9 (8 signals missing due to overlap). LCMS (ESI) for $C_{16}H_{18}ClN_4OS$ (M+H)$^+$: calcd. 349.1, obsvd. 349.1.

4-Chloro-2-[4-(4-chloro-phenyl)-piperazin-1-yl]-6,7-dihydro-thieno[3,2-d]pyrimidine (3a)

Charge 2-[4-(4-Chloro-phenyl)-piperazin-1-yl]-6,7-dihydro-thieno[3,2-d]pyrimidin-4-ol (4a, 50.4 g) into an inerted, dry jacketed reactor equipped with a mechanical stirrer, thermocouple thermometer, dropping funnel and $N_2$ line. Charge acetonitrile (250 mL) into the reactor followed by $POCl_3$ (14.8 mL) keeping the temperature at 25-35° C. Stir at 60° C. for 4-6 h and then bring the internal temperature to 23±2° C. In a different reactor prepare a 2N NaOH (approx. 250 mL) aqueous solution. Pour the contents of the first reactor into the reactor containing the 2N NaOH keeping the temperature below 20° C. Stir the above mixture at 23±2° C. for 16 h and collect the solid by filtration. Wash the cake with water 3-5 times (approx. 50 mL per wash), air-dry (suction) the cake for 3-4 h and then continue drying in a vacuum oven at 50° C. for a minimum of 16 h. Transfer the resulting solid (96.0 g, 95%) into a suitable container and store under nitrogen or argon. NMR (400 MHz, $CDCl_3$) δ 7.18-7.26 (m, 2H), 6.82-6.93 (m, 2H), 3.88-3.94 (m, 4H), 3.22-3.36 (m, 4H), 3.15-3.21 (m, 4H); $^{13}$C NMR (400 MHz, $CDCl_3$) δ 172.8, 160.4, 152.9, 150.1, 129.4, 125.4, 119.8, 118.1, 77.6, 49.6, 44.4, 38.0, 29.3 (4 signals missing due to overlap); LCMS (ESI) for $C_{16}H_{17}Cl_2N_4S$ (M+H)$^+$: calcd. 367.1, obsvd. 367.0.

(R)-4-Chloro-2-[4-(4-chloro-phenyl)-piperazin-1-yl]-6,7-dihydro-thieno[3,2-d]pyrimidine 5-oxide (2a)

Using a jacketed reactor with mechanical stirring at 400 rpm, charge (S)-Hydrobenzoin (292 mg) and toluene (50 mL), followed by Ti(i-PrO)$_4$ (0.20 mL) and water (0.25 mL). Stir the mixture at 20° C. for 30 min. then charge 4-Chloro-2-[4-(4-chloro-phenyl)-piperazin-1-yl]-6,7-dihydro-thieno [3,2-d]pyrimidine (3a, 5.00 g) and stir the mixture for 15 min at 20° C. before being cooling to 0° C. (it took 20 min). Charge TBHP (70% aqueous) (0.75 mL) to the reaction mixture and stir for 23 h at 0° C. Reaction reached 96% conversion and 89% ee. Quench with 5% $Na_2SO_3$ (20 mL). Separate the layers and extract the aqueous layer with dichloromethane (50 mL). Combine organic layers and wash with water (20 mL), dry ($MgSO_4$), filter, and concentrate affording the desired sulfoxide in (4.6 g, 88% yield, 89% ee). The product may be recrystallized from THF/water (5:1) with good recovery to yield material >96% ee. NMR (400 MHz, $CDCl_3$) δ 7.16-7.26 (m, 2H), 6.80-6.90 (m, 2H), 3.90-4.20 (m, 4H), 3.75-3.90 (m, 1H), 3.00-3.30 (m, 7H); $^{13}$C NMR (400 MHz, $CDCl_3$) δ 177.5, 162.5, 160.7, 149.8, 129.4, 125.7, 123.9, 118.2, 49.6, 46.5, 44.7, 44.4, 33.7 (3 signals missing due to overlap); LCMS (ESI) for $C_{16}H_{17}Cl_2N_4OS$ (M+H)$^+$: calcd. 383.1, obsvd. 383.0.

Further Examples

The following compounds are prepared by the amination of (R)-4-chloro-2-[4-(4-chloro-phenyl)-piperazin-1-yl]-6,7-dihydro-thieno[3,2-d]pyrimidine-5-oxide (2), described above, with various amines or amino acids, as detailed below.

(R)-2-{(R)-2-[4-(4-Chloro-phenyl)-piperazin-1-yl]-5-oxo-6,7-dihydro-5H-5λ$^4$-thieno[3,2-d]pyrimidin-4-ylamino}-3-methyl-butyric acid methyl ester

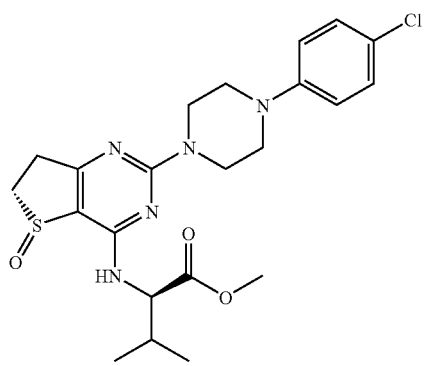

The procedure for the formation of (R)-2-{(R)-2-[4-(4-chloro-phenyl)-piperazin-1-yl]-5-oxo-6,7-dihydro-5H-5λ$^4$-thieno[3,2-d]pyrimidin-4-ylamino}-3-methyl-butan-1-ol (with the exception of omitting the IPA recrystallization) was followed, starting with (R)-4-chloro-2-[4-(4-chloro-phenyl)-piperazin-1-yl]-6,7-dihydro-thieno[3,2-d]pyrimidine-5-oxide and D-valine methyl ester (1.3 equiv). This resulted in the crude product being obtained in 85% yield. $^1$H NMR (500 MHz, CDCl$_3$) δ 7.18-7.26 (m, 2H), 6.82-6.90 (m, 2H), 5.78 (d, J=6.5 Hz, 1H), 4.59 (dd, J=7.0, 7.0 Hz, 1H), 3.98 (bs, 4H), 3.72 (s, 3H), 3.62 (ddd, J=7.5, 7.5, 15.0 Hz, 1H), 3.36 (ddd, J=8.0, 8.0, 15.0 Hz, 1H), 3.10-3.20 (m, 4H), 2.95-3.10 (m, 2H), 2.23 (m, 1H), 1.00-1.07 (m, 6H); $^{13}$C NMR (500 MHz, CDCl$_3$) δ 174.8, 172.8, 163.1, 159.8, 150.2, 129.4, 125.4, 118.0, 109.0, 59.6, 59.5, 52.3, 50.4, 49.7, 44.1, 33.0, 31.3, 19.4, 19.1 (3 signals missing due to overlap). LCMS (ESI) for C$_{22}$H$_{29}$ClN$_5$O$_3$S (M+H)$^+$: calcd. 478.2, obsvd. 478.1.

(R)-2-{(R)-2-[4-(4-Chloro-phenyl)-piperazin-1-yl]-5-oxo-6,7-dihydro-5H-5λ$^4$-thieno[3,2-d]pyrimidin-4-ylamino}-3-methyl-butan-1-ol

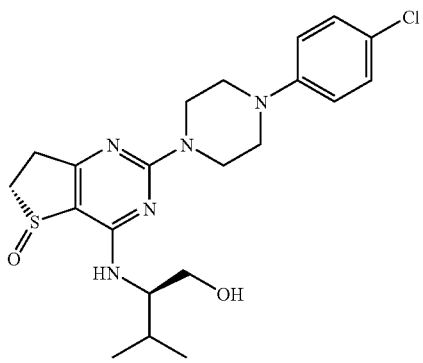

Charge (R)-4-Chloro-2-[4-(4-chloro-phenyl)-piperazin-1-yl]-6,7-dihydro-thieno[3,2-d]pyrimidine-5-oxide (0.10 g), D-valinol (46.8 mg,), and DMSO (2 mL) to a 3 neck round bottom flask with temp. probe, nitrogen inlet and stir bar. Charge diisopropylethylamine (0.1 mL) and heat the mixture to 80° C. with stirring for 2 h. Cool the mixture to ambient temperature and charge water slowly (3-5 mL) which precipitates the product as an off-white solid. Filter the solid and rinse it with water. Dry the solid for 12 h at 50° C. under vacuum providing (R)-2-{(R)-2-[4-(4-Chloro-phenyl)-piperazin-1-yl]-5-oxo-6,7-dihydro-5H-5λ$^4$-thieno[3,2-d]pyrimidin-4-ylamino}-3-methyl-butan-1-ol (0.21 g, 92% yld.) as a off-white solid. Recrystallize from IPA/H$_2$O (15 vols/0.5 vols) to give material of >99% purity. $^1$H NMR (400 MHz, CDCl$_3$) δ 7.16-7.26 (m, 2H), 7.00 (bs, 1H), 6.80-6.90 (m, 2H), 4.02-4.12 (m, 1H), 3.90-4.00 (m, 4H), 3.68-3.85 (m, 3H), 3.55-3.65 (m, 1H), 3.35-3.45 (m, 1H), 3.12-3.20 (m, 4H), 2.94-3.08 (m, 2H), 1.92-2.06 (m, 1H), 0.95 (d, J=6.5 Hz, 3H), 0.90 (d, J=6.5 Hz, 3H); $^{13}$C NMR (400 MHz, CDCl$_3$) δ 174.6, 163.1, 160.4, 150.1, 129.4, 125.3, 118.0, 107.6, 63.9, 58.6, 49.6, 44.1, 33.0, 29.7, 20.2, 19.8 (5 signals missing due to overlap); LCMS (ESI) for C$_{21}$H$_{29}$ClN$_5$O$_2$S (M+H)$^+$: calcd. 450.2, obsvd. 450.1.

{(R)-2-[4-(4-Chloro-phenyl)-piperazin-1-yl]-5-oxo-6,7-dihydro-5H-5λ$^4$-thieno[3,2-d]pyrimidin-4-yl}-((S)-1-phenyl-ethyl)-amine

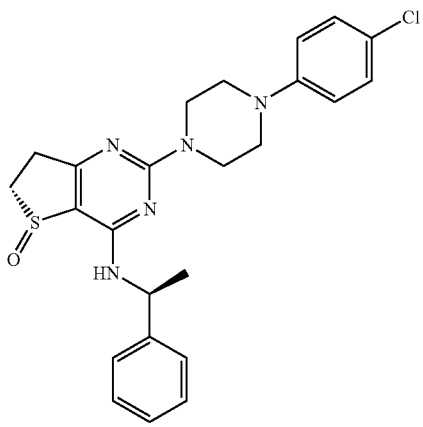

The procedure for the formation of (R)-2-{(R)-2-[4-(4-chloro-phenyl)-piperazin-1-yl]-5-oxo-6,7-dihydro-5H-5λ$^4$-thieno[3,2-d]pyrimidin-4-ylamino}-3-methyl-butan-1-ol (with the IPA/H$_2$O recrystallization being replaced with an IPA/H$_2$O rinses) was followed, starting with (R)-4-chloro-2-[4-(4-chloro-phenyl)-piperazin-1-yl]-6,7-dihydro-thieno[3,2-d]pyrimidine-5-oxide and (S)-Methyl-benzylamine. This resulted in a purified product being obtained in a 57% yield. $^1$H NMR (400 MHz, CDCl$_3$) δ 7.18-7.28 (m, 4H), 7.05-7.17 (m, 3H), 6.80-6.90 (m, 2H), 6.52 (d, J=5.6 Hz, 1H), 5.19 (dddd, J=7.0, 7.0, 7.0, 7.0 Hz, 1H), 3.80-4.00 (m, 4H), 3.58 (ddd, J=8.0, 8.0, 16.0 Hz, 1H), 3.34 (ddd, J=8.0, 8.0, 16.0 Hz, 1H), 2.90-3.20 (m, 6H), 1.55 (d, J=7.2 Hz, 3H); $^{13}$C NMR (400 MHz, CDCl$_3$) δ 174.6, 163.2, 159.2, 150.2, 144.4, 129.4, 128.6, 127.1, 126.3, 125.3, 118.0, 108.5, 51.1, 50.2, 49.6, 44.1, 33.0, 23.2 (6 signals missing due to overlap); LCMS (ESI) for C$_{24}$H$_{27}$ClN$_5$OS (M+H)$^+$: calcd. 468.2, obsvd. 468.3.

{(R)-2-[4-(4-Chloro-phenyl)-piperazin-1-yl]-5-oxo-6,7-dihydro-5H-5λ$^4$-thieno[3,2-d]pyrimidin-4-yl}-cyclohexyl-amine

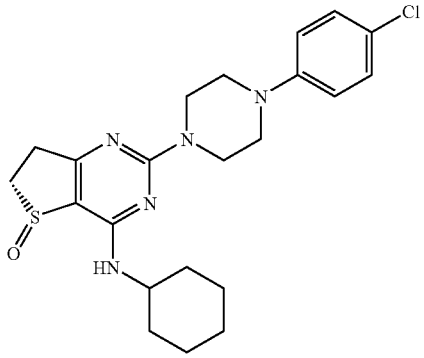

The procedure for the formation of (R)-2-{(R)-2-[4-(4-chloro-phenyl)-piperazin-1-yl]-5-oxo-6,7-dihydro-5H-5λ⁴-thieno[3,2-d]pyrimidin-4-ylamino}-3-methyl-butan-1-ol (with the IPA/H₂O recrystallization was replaced by IPA/H₂O rinses) was followed, starting with (R)-4-chloro-2-[4-(4-chloro-phenyl)-piperazin-1-yl]-6,7-dihydro-thieno[3,2-d]pyrimidine-5-oxide and cyclohexylamine. The purified product was obtained in a 77% yield. ¹H NMR (400 MHz, CDCl₃) δ 7.18-7.24 (m, 2H), 6.80-6.90 (m, 2H), 5.77 (d, J=7.2 Hz, 1H), 3.88-4.02 (m, 5H), 3.58 (ddd, J=7.5, 7.5, 15.0 Hz, 1H), 3.31 (ddd, J=8.0, 8.0, 15.5 Hz, 1H), 3.12-3.22 (m, 4H), 2.90-3.06 (m, 2H), 1.10-2.00 (m, 10H); ¹³C NMR (400 MHz, CDCl₃) δ 174.3, 163.4, 159.3, 150.2, 129.3, 125.3, 118.0, 108.5, 50.1, 50.0, 49.6, 44.1, 33.1, 33.0, 32.8, 25.9, 25.4, 25.3 (4 signals missing due to overlap); LCMS (ESI) for $C_{22}H_{29}ClN_5OS$ (M+H)⁺: calcd. 446.2, obsvd. 446.2.

(R)-2-[4-(4-Chloro-phenyl)-piperazin-1-yl]-4-piperidin-1-yl-6,7-dihydro-thieno[3,2-d]pyrimidine 5-oxide

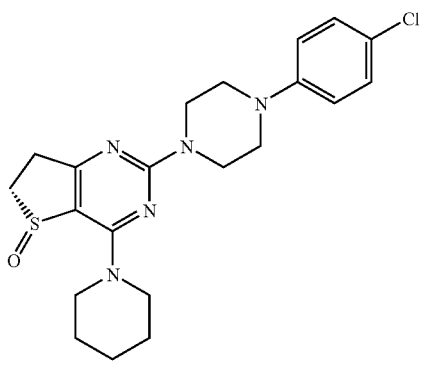

The procedure for the formation of (R)-2-{(R)-2-[4-(4-chloro-phenyl)-piperazin-1-yl]-5-oxo-6,7-dihydro-5H-5λ⁴-thieno[3,2-d]pyrimidin-4-ylamino}-3-methyl-butan-1-ol (with the IPA/H₂O recrystallization replaced with IPA/H₂O rinses) was followed starting with (R)-4-chloro-2-[4-(4-chloro-phenyl)-piperazin-1-yl]-6,7-dihydro-thieno[3,2-d]pyrimidine-5-oxide and piperidine. The purified product was obtained in a 61% yield. ¹H NMR (400 MHz, CDCl₃) δ 7.18-7.24 (m, 2H), 6.80-6.90 (m, 2H), 3.95-4.00 (m, 4H), 3.80-3.95 (m, 4H), 3.68 (ddd, J=8.0, 8.0, 16.0 Hz, 1H), 3.13-3.20 (m, 4H), 2.96-3.13 (m, 3H), 1.60-1.80 (m, 6H); ¹³C NMR (400 MHz, CDCL₃) δ 177.7, 162.3, 159.9, 150.2, 129.4, 125.3, 118.0, 109.8, 49.7, 48.3, 48.0, 44.1, 32.8, 26.1, 24.9 (6 signals missing due to overlap); LCMS (ESI) for $C_{21}H_{27}ClN_5OS$ (M+H)⁺: calcd. 432.2, obsvd. 432.3.

Other examples of dihydrothienopyrimidine compounds that can be prepared analogously to the methods of synthesis described herein are found in U.S. publication no. 2008/0096882A1, which is incorporated by reference in its entirety. These compounds are suitable as PDE4-inhibitors and have IC₅₀ values of less than or equal to 1 μmol.

We claim:
1. A method for preparing intermediates of formula 6

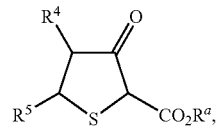

6 comprising the steps of:
a. reacting reagents of the formulas HS—CH₂—CO₂R^a and CHR⁵=CR⁴—CO₂R^a to obtain an intermediate of formula 7:

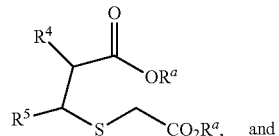

7 and b. cyclizing the intermediate of formula 7 in a solvent and in the presence of TiCl₃(OiPr) or a chiral variant of TiCl₃(OiPr) selected from the group consisting of 1,1'-bi-2-naphthol (BINOL), a substituted BINOL, a chiral diol, 1,1'-binaphthalene-(2,2'-diyl)bis(diphenylphosphine) (BINAP), a compound substituted with 2,5-alkyl-substituted phospholane rings (a DuPhos compound), α,α,α',α'-tetraaryl-1,3-dioxolan-4,5-dimethanol (Taddol), and a tartrate, and in the presence of an amine base to obtain the intermediate of formula 6, wherein:

R⁴ and R⁵ are each independently H, $C_{1-6}$-alkyl, $C_{2-6}$-alkenyl, $C_{2-6}$-alkynyl, $C_{6-10}$-aryl, $C_{6-10}$-aryl-$C_{1-6}$-alkylene, $C_{1-5}$-heteroaryl-$C_{1-6}$-alkylene, $C_{3-10}$ heterocycle, $C_{5-10}$-heteroaryl, —O—$C_{1-6}$-alkyl, —O—$C_{6-10}$-aryl, —O—$C_{3-10}$ heterocycle, —O—$C_{5-10}$-heteroaryl, —NR'R", fluoro, $C_{1-6}$-fluoroalkyl, or $C_{1-6}$-fluoroalkoxy, and wherein R' and R" are each independently H or $C_{1-6}$-alkyl, and wherein each group is optionally substituted by one or more groups selected from OH, oxo, halogen, $C_{1-6}$-alkyl, and O—$C_{1-6}$-alkyl; and R^a is $C_{1-10}$-alkyl.

2. The method according to claim 1, wherein R^a is $C_{1-6}$-alkyl.

3. The method according to claim 1, wherein in the cyclization step (b), the amine base is diisopropylethylamine or triethylamine.

4. A method for preparing intermediates of formula 6

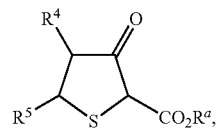

6 comprising the steps of:
a. reacting reagents of the formulas HS—CH$_2$—CO$_2$R$^a$ and CHR$^5$=CR$^4$—CO$_2$R$^a$ to obtain an intermediate of formula 7:

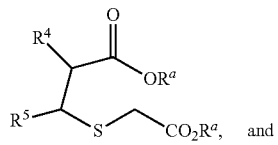

7 b. cyclizing the intermediate of formula 7 in a solvent in the presence of:
(i) SnX$_4$, CuX$_2$, or NiX$_2$, wherein X is Cl, Br, or OTf,
(ii) TiCl$_3$(OiPr), or a chiral variant thereof, and
(iii) an amine base,
to obtain the intermediate of formula 6, wherein:
R$^4$ and R$^5$ are each independently H, C$_{1-6}$-alkyl, C$_{2-6}$-alkenyl, C$_{2-6}$-alkynyl, C$_{6-10}$-aryl, C$_{6-10}$-aryl-C$_{1-6}$-alkylene, C$_{5-10}$-heteroaryl-C$_{1-6}$-alkylene, C$_{3-10}$ heterocycle, C$_{5-10}$-heteroaryl, —O—C$_{1-6}$-alkyl, —O—C$_{6-10}$-aryl, —O—C$_{3-10}$ heterocycle, —O—C$_{5-10}$-heteroaryl, —NR'R'', fluoro, C$_{1-6}$-fluoroalkyl, or C$_{1-6}$-fluoroalkoxy, and wherein R' and R'' are each independently H or C$_{1-6}$-alkyl, and wherein each group is optionally substituted by one or more groups selected from OH, oxo, halogen, C$_{1-6}$-alkyl, and O—C$_{1-6}$-alkyl; and R$^a$ is C$_{1-10}$-alkyl.

5. The method according to claim 1, wherein the cyclization step (b) is performed in the presence of SnX$_4$, CuX$_2$, or NiX$_2$, wherein X is Cl, Br, or OTf.

6. The method according to claim 1, wherein the solvent is an alcoholic solvent.

7. The method according to claim 1, wherein the cyclization step (b) is carried out at a temperature between 0° C. and −78° C.

8. The method according to claim 4, wherein R$^a$ is C$_{1-6}$-alkyl.

9. The method according to claim 4, wherein in the cyclization step (b), the amine base is diisopropylethylamine or triethylamine.

10. The method according to claim 4, wherein the solvent is an alcoholic solvent.

11. The method according to claim 4, wherein the cyclization step (b) is carried out at a temperature between 0° C. and −78° C.

* * * * *